United States Patent
Dunkel et al.

(10) Patent No.: US 7,799,739 B2
(45) Date of Patent: Sep. 21, 2010

(54) BIPHENYLCARBOXAMIDES FOR CONTROLLING MICRO-ORGANISMS

(75) Inventors: Ralf Dunkel, Lyons (FR); Hans-Ludwig Elbe, Wuppertal (DE); Jörg Nico Greul, Leichlingen (DE); Herbert Gayer, Monheim (DE); Arnd Voerste, Köln (DE); Ulrike Wachendorff-Neumann, Neuwied (DE); Peter Dahmen, Neuss (DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 12/097,753

(22) PCT Filed: Dec. 5, 2006

(86) PCT No.: PCT/EP2006/011652

§ 371 (c)(1),
(2), (4) Date: Nov. 3, 2008

(87) PCT Pub. No.: WO2007/068376

PCT Pub. Date: Jun. 21, 2007

(65) Prior Publication Data

US 2009/0076113 A1    Mar. 19, 2009

(30) Foreign Application Priority Data

Dec. 17, 2005  (DE) .................. 10 2005 060 462 U

(51) Int. Cl.
- A01N 43/56  (2006.01)
- C07D 231/14  (2006.01)
- C07C 271/10  (2006.01)
- C07C 229/52  (2006.01)
- C07C 223/06  (2006.01)

(52) U.S. Cl. ..................... 504/280; 548/374.1; 560/27; 560/43; 568/424

(58) Field of Classification Search ................. 514/406, 514/539, 650; 548/374.1; 560/43, 27; 568/306
See application file for complete search history.

(56) References Cited

U.S. PATENT DOCUMENTS

| | | | |
|---|---|---|---|
| 5,093,347 A | 3/1992 | Graneto et al. | |
| 5,922,732 A | 7/1999 | Urch et al. | |
| 5,998,450 A | 12/1999 | Eicken et al. | |
| 6,369,093 B1 | 4/2002 | Elbe et al. | |
| 7,098,227 B2 * | 8/2006 | Dunkel et al. | 514/365 |
| 7,186,862 B2 * | 3/2007 | Rieck et al. | 564/184 |
| 7,329,633 B2 * | 2/2008 | Dunkel et al. | 504/280 |
| 7,381,688 B2 * | 6/2008 | Dunkel et al. | 504/289 |
| 7,388,097 B2 * | 6/2008 | Elbe et al. | 548/136 |
| 7,521,397 B2 * | 4/2009 | Dunkel et al. | 504/280 |
| 2002/0061913 A1 | 5/2002 | Urch et al. | |
| 2002/0171490 A1 | 11/2002 | Chimura | |
| 2004/0049035 A1 | 3/2004 | Walter et al. | |

FOREIGN PATENT DOCUMENTS

| | | |
|---|---|---|
| EP | 0545 099 A2 | 6/1993 |
| JP | 01-290662 | 11/1989 |
| WO | WO-9637494 | 11/1996 |
| WO | WO-9825923 | 6/1998 |
| WO | WO-01/53259 | 7/2001 |
| WO | WO-0149664 | 7/2001 |
| WO | WO 03/070705 A1 | 8/2003 |
| WO | WO 2005/063710 A1 * | 7/2005 |
| WO | WO 2005063710 | 7/2005 |

* cited by examiner

Primary Examiner—Kamal A Saeed
Assistant Examiner—Kristin Bianchi
(74) Attorney, Agent, or Firm—Baker Donelson Bearman, Caldwell & Berkowitz, PC

(57) ABSTRACT

Novel biphenylcarboxamides of the formula (I)

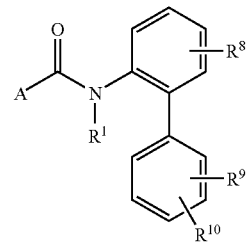

(I)

There is further provided a plurality of processes for preparing these compounds and their use for controlling unwanted microorganisms, and also novel intermediates and their preparation.

10 Claims, No Drawings

BIPHENYLCARBOXAMIDES FOR CONTROLLING MICRO-ORGANISMS

CROSS REFERENCE TO RELATED APPLICATIONS

This application is a §371 National Stage Application of PCT/EP2006/011652 filed Dec. 5, 2006 which claims priority from German Application 10 2005 060 462.5 filed Dec. 17, 2005, the content of which is incorporated by reference.

BACKGROUND OF THE INVENTION

1. Field of the Invention

The present invention relates to novel biphenylcarboxamides, to a plurality of processes for their preparation and to their use for controlling harmful microorganisms in crop protection and in the protection of materials.

2. Description of Related Art

It is already known that certain biphenylcarboxamides have fungicidal properties (cf., for example, WO 03/070705 and EP-A 0 545 099). The activity of the compounds described in these publications is good; however, it is sometimes unsatisfactory.

SUMMARY OF THE INVENTION

This invention now provides novel biphenylcarboxamides of the formula (I)

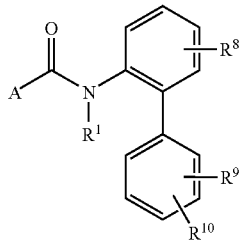

(I)

in which $R^1$ represents hydrogen, $C_1$-$C_8$-alkyl, $C_1$-$C_6$-alkylsulphinyl, $C_1$-$C_6$-alkylsulphonyl, $C_1$-$C_4$-alkoxy-$C_1$-$C_4$-alkyl, $C_3$-$C_8$-cycloalkyl; $C_1$-$C_6$-haloalkyl, $C_1$-$C_4$-haloalkylthio, $C_1$-$C_4$-haloalkyl-sulphinyl, $C_1$-$C_4$-haloalkylsulphonyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$-alkyl)carbonyl-$C_1$-$C_3$-alkyl, halo-($C_1$-$C_3$-alkoxy)carbonyl-$C_1$-$C_3$-alkyl having in each case 1 to 13 fluorine, chlorine and/or bromine atoms;

($C_1$-$C_8$-alkyl)carbonyl, ($C_1$-$C_8$-alkoxy)carbonyl, ($C_1$-$C_8$-alkylthio)carbonyl, ($C_1$-$C_4$-alkoxy-$C_1$-$C_4$-alkyl)carbonyl, ($C_3$-$C_6$-alkenyloxy)carbonyl, ($C_3$-$C_6$-alkynyloxy)carbonyl, ($C_3$-$C_8$-cycloalkyl)carbonyl; ($C_1$-$C_6$-haloalkyl)carbonyl, ($C_1$-$C_6$-haloalkoxy)carbonyl, ($C_3$-$C_6$-haloalkylthio)carbonyl, (halo-$C_1$-$C_4$-alkoxy-$C_1$-$C_4$-alkyl)carbonyl, ($C_3$-$C_6$-haloalkenyloxy)-carbonyl, ($C_3$-$C_6$-haloalkynyloxy)carbonyl, ($C_3$-$C_8$-halocycloalkyl)carbonyl having in each case 1 to 9 fluorine, chlorine and/or bromine atoms; or —$CH_2$—C≡C—$R^{1-A}$, —$CH_2$—CH=CH—$R^{1-A}$, —CH=C=CH—$R^{1-A}$, —C(=O)C(=O)$R^2$, —CONR$^3$R$^4$ or —$CH_2$NR$^5$R$^6$, $R^{1-A}$ represents hydrogen, $C_1$-$C_6$-alkyl, $C_1$-$C_6$-haloalkyl, $C_2$-$C_6$-alkenyl, $C_2$-$C_6$-alkynyl, $C_3$-$C_7$-cycloalkyl, ($C_1$-$C_4$-alkoxy)carbonyl, ($C_3$-$C_6$-alkenyloxy)carbonyl, ($C_3$-$C_6$-alkynyloxy)carbonyl or cyano, $R^2$ represents hydrogen, $C_1$-$C_8$-alkyl, $C_1$-$C_8$-alkoxy, $C_1$-$C_4$-alkoxy-$C_1$-$C_4$-alkyl, $C_3$-$C_8$-cycloalkyl; $C_1$-$C_6$-haloalkyl, $C_1$-$C_6$-haloalkoxy, halo-$C_1$-$C_4$-alkoxy-$C_1$-$C_4$-alkyl, $C_3$-$C_8$-halocycloalkyl having in each case 1 to 9 fluorine, chlorine and/or bromine atoms, $R^3$ and $R^4$ independently of one another each represent hydrogen, $C_1$-$C_8$-alkyl, $C_1$-$C_4$-alkoxy-$C_1$-$C_4$-alkyl, $C_3$-$C_8$-cycloalkyl; $C_1$-$C_8$-haloalkyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms, $R^3$ and $R^4$ furthermore together with the nitrogen atom to which they are attached form a saturated heterocycle which is optionally mono- or polysubstituted by identical or different substituents from the group consisting of halogen and $C_1$-$C_4$-alkyl and which has 5 to 8 ring atoms, where the heterocycle may contain 1 or 2 further non-adjacent heteroatoms from the group consisting of oxygen, sulphur and NR$^7$, $R^5$ and $R^6$ independently of one another each represent hydrogen, $C_1$-$C_8$-alkyl, $C_3$-$C_8$-cycloalkyl; $C_1$-$C_8$-haloalkyl, $C_3$-$C_8$-halocycloalkyl having in each case 1 to 9 fluorine, chlorine and/or bromine atoms, $R^5$ and $R^6$ furthermore together with the nitrogen atom to which they are attached form a saturated heterocycle which is optionally mono- or polysubstituted by identical or different substituents from the group consisting of halogen and $C_1$-$C_4$-alkyl and which has 5 to 8 ring atoms, where the heterocycle may contain 1 or 2 further non-adjacent heteroatoms from the group consisting of oxygen, sulphur and NR$^7$, $R^7$ represents hydrogen or $C_1$-$C_6$-alkyl, $R^8$ represents hydrogen or fluorine, $R^9$ represents —SO$_m$R$^{11}$, —SO$_2$NR$^{12}$R$^{13}$, —C(=X)R$^{14}$, Si(R$^{15}$)$_3$, —NR$^{12}$R$^{13}$, —CH$_2$—NR$^{12}$R$^{13}$, $R^{10}$ represents fluorine, chlorine, bromine, iodine, methyl or trifluoromethyl, $R^{11}$ represents $C_1$-$C_6$-alkyl or $C_1$-$C_6$-haloalkyl having 1 to 13 halogen atoms, m represents 1 or 2, $R^{12}$ represents hydrogen, $C_1$-$C_4$-alkyl or —C(=x)R$^{14}$, $R^{13}$ represents hydrogen, $C_1$-$C_4$-alkyl or —C(=X)R$^{14}$, $R^{12}$ and $R^{13}$ furthermore together with the nitrogen atom to which they are attached form a saturated heterocycle which is optionally mono- or polysubstituted by identical or different substituents from the group consisting of halogen and $C_1$-$C_4$-alkyl and which has 5 to 8 ring atoms, where the heterocycle may contain 1 or 2 further non-adjacent heteroatoms from the group consisting of oxygen, sulphur and NR$^7$, X represents O (oxygen) or S (sulphur), $R^{14}$ represents hydrogen, $C_1$-$C_4$-alkyl, $C_1$-$C_4$-alkoxy or —NR$^{16}$R$^{17}$, $R^{15}$ represents hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylthio-$C_1$-$C_4$-alkyl or $C_1$-$C_6$-haloalkyl, where the three radicals R$^{15}$ may each be identical or different, $R^{16}$ hydrogen or $C_1$-$C_4$-alkyl, $R^{17}$ hydrogen or $C_1$-$C_4$-alkyl, $R^{16}$ and $R^{17}$ furthermore together with the nitrogen atom to which they are attached form a saturated heterocycle which is optionally mono- or polysubstituted by identical or different substituents from the group consisting of halogen and $C_1$-$C_4$-alkyl and which has 5 to 8 ring atoms, where the heterocycle may contain 1 or 2 further non-adjacent heteroatoms from the group consisting of oxygen, sulphur and NR$^7$, A represents one of the radicals A1 to A19 below

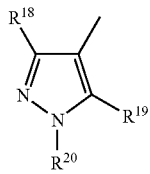 A1

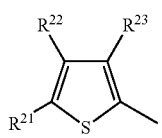 A2

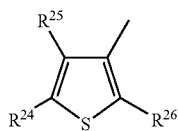 A3

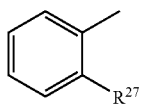 A4

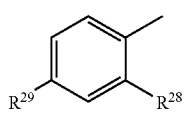 A5

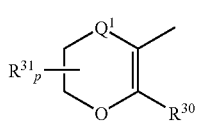 A6

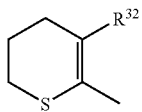 A7

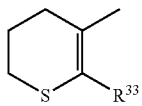 A8

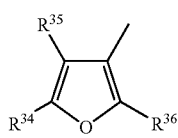 A9

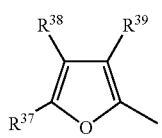 A10

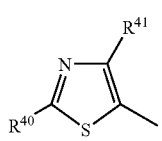 A11

-continued

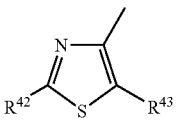 A12

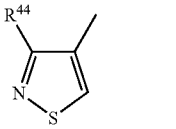 A13

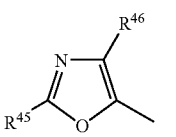 A14

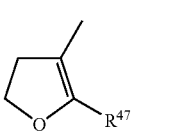 A15

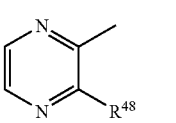 A16

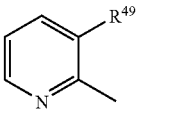 A17

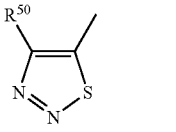 A18

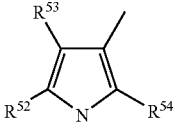 A19

$R^{18}$ represents hydrogen, cyano, halogen, nitro, $C_1$-$C_4$-alkyl, $C_1$-$C_4$-alkoxy, $C_1$-$C_4$-alkylthio, $C_3$-$C_6$-cycloalkyl, $C_1$-$C_4$-haloalkyl, $C_1$-$C_4$-haloalkoxy or $C_1$-$C_4$-haloalkylthio having in each case 1 to 5 halogen atoms, aminocarbonyl or aminocarbonyl-$C_1$-$C_4$-alkyl, $R^{19}$ represents hydrogen, halogen, cyano, $C_1$-$C_4$-alkyl, $C_1$-$C_4$-alkoxy or $C_1$-$C_4$-alkylthio, $R^{20}$ represents hydrogen, $C_1$-$C_4$-alkyl, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, $C_1$-$C_4$-alkoxy-$C_1$-$C_4$-alkyl, $C_1$-$C_4$-haloalkyl, $C_1$-$C_4$-haloalkylthio-$C_1$-$C_4$-alkyl, $C_1$-$C_4$-haloalkoxy-$C_1$-$C_4$-alkyl having in each case 1 to 5 halogen atoms, or phenyl, $R^{21}$ and $R^{22}$ independently of one another represent hydrogen, halogen, $C_1$-$C_4$-alkyl or $C_1$-$C_4$-haloalkyl having 1 to 5 halogen atoms, $R^{23}$ represents halogen, cyano or $C_1$-$C_4$-alkyl, or $C_1$-$C_4$-haloalkyl or $C_1$-$C_4$-haloalkoxy having in each case 1 to 5 halogen atoms, $R^{24}$ and $R^{25}$ independently of one another represent hydrogen, halogen, $C_1$-$C_4$-alkyl or $C_1$-$C_4$-haloalkyl having 1 to 5 halogen atoms, $R^{26}$ represents hydrogen, halogen, $C_1$-$C_4$-alkyl or $C_1$-$C_4$-haloalkyl having 1 to 5 halogen atoms, $R^{27}$ represents hydrogen, halogen, hydroxyl, cyano, $C_1$-$C_6$-alkyl, $C_1$-$C_4$-haloalkyl, $C_1$-$C_4$-haloalkoxy or $C_1$-$C_4$-haloalkylthio having in each case 1 to 5 halogen atoms, $R^{28}$ represents halogen, hydroxyl, cyano, $C_1$-$C_4$-alkyl, $C_1$-$C_4$-alkoxy, $C_1$-$C_4$-alkylthio, $C_1$-$C_4$-haloalkyl, $C_1$-$C_4$-haloalkylthio or $C_1$-$C_4$-haloalkoxy having in each case 1 to 5 halogen atoms, $R^{29}$ represents hydrogen, halogen, cyano, $C_1$-$C_4$-alkyl, $C_1$-$C_4$-alkoxy, $C_1$-$C_4$-alkylthio, $C_1$-$C_4$-haloalkyl, $C_1$-$C_4$-haloalkoxy having in each case 1 to 5 halogen atoms, $C_1$-$C_4$-alkylsulphinyl or $C_1$-$C_4$-alkylsulphonyl, $R^{30}$ represents $C_1$-$C_4$-alkyl or $C_1$-$C_4$-haloalkyl having 1 to 5 halogen atoms, $R^{31}$ represents $C_1$-$C_4$-alkyl, $Q^1$ represents S (sulphur), SO, $SO_2$ or $CH_2$, p represents 0, 1 or 2, where $R^{22}$ represents identical or different radicals if p represents 2, $R^{32}$ represents $C_1$-$C_4$-alkyl or $C_1$-$C_4$-haloalkyl having 1 to 5 halogen atoms, $R^{33}$ represents $C_1$-$C_4$-alkyl or $C_1$-$C_4$-haloalkyl having 1 to 5 halogen atoms, $R^{34}$ and $R^{35}$ independently of one another represent hydrogen, halogen, amino, $C_1$-$C_4$-alkyl or $C_1$-$C_4$-haloalkyl having 1 to 5 halogen atoms, $R^{36}$ represents hydrogen, halogen, $C_1$-$C_4$-alkyl or $C_1$-$C_4$-haloalkyl having 1 to 5 halogen atoms, $R^{37}$ and $R^{33}$ independently of one another represent hydrogen, halogen, amino, nitro, $C_1$-$C_4$-alkyl or $C_1$-$C_4$-haloalkyl having 1 to 5 halogen atoms, $R^{39}$ represents hydrogen, halogen, $C_1$-$C_4$-alkyl or $C_1$-$C_4$-haloalkyl having 1 to 5 halogen atoms, $R^{40}$ represents hydrogen, halogen, amino, $C_1$-$C_4$-alkylamino, di-($C_1$-$C_4$-alkyl)amino, cyano, $C_1$-$C_4$-alkyl or $C_1$-$C_4$-haloalkyl having 1 to 5 halogen atoms, $R^{41}$ represents halogen, $C_1$-$C_4$-alkyl or $C_1$-$C_4$-haloalkyl having 1 to 5 halogen atoms, $R^{42}$ represents hydrogen, halogen, amino, $C_1$-$C_4$-alkylamino, di-($C_1$-$C_4$-alkyl)amino, cyano, $C_1$-$C_4$-alkyl or $C_1$-$C_4$-haloalkyl having 1 to 5 halogen atoms, $R^{43}$ represents halogen, $C_1$-$C_4$-alkyl or $C_1$-$C_4$-haloalkyl having 1 to 5 halogen atoms, $R^{44}$ represents halogen, $C_1$-$C_4$-alkyl or $C_1$-$C_4$-haloalkyl having 1 to 5 halogen atoms, $R^{45}$ represents hydrogen or $C_1$-$C_4$-alkyl, $R^{46}$ represents halogen or $C_1$-$C_4$-alkyl, $R^{47}$ represents $C_1$-$C_4$-alkyl or $C_1$-$C_4$-haloalkyl having 1 to 5 halogen atoms, $R^{48}$ represents hydrogen, halogen, $C_1$-$C_4$-alkyl or $C_1$-$C_4$-haloalkyl having 1 to 5 halogen atoms, $R^{49}$ represents halogen, hydroxyl, $C_1$-$C_4$-alkyl, $C_1$-$C_4$-alkoxy, $C_1$-$C_4$-alkylthio, $C_1$-$C_4$-haloalkyl, $C_1$-$C_4$-haloalkylthio or $C_1$-$C_4$-haloalkoxy having in each case 1 to 5 halogen atoms, $R^{50}$ represents $C_1$-$C_4$-alkyl, $R^{51}$ represents hydrogen, cyano, $C_1$-$C_4$-alkyl, $C_1$-$C_4$-haloalkyl having 1 to 5 halogen atoms, $C_1$-$C_4$-alkoxy-$C_1$-$C_4$-alkyl, hydroxy-$C_1$-$C_4$-alkyl, $C_1$-$C_4$-alkylsulphonyl, di($C_1$-$C_4$-alkyl)aminosulphonyl, $C_1$-$C_6$-alkylcarbonyl or in each case optionally substituted phenylsulphonyl or benzoyl, $R^{52}$ represents hydrogen, halogen, $C_1$-$C_4$-alkyl or $C_1$-$C_4$-haloalkyl having 1 to 5 halogen atoms, $R^{53}$ represents hydrogen, halogen, cyano, $C_1$-$C_4$-alkyl or $C_1$-$C_4$-haloalkyl having 1 to 5 halogen atoms, $R^{54}$ represents hydrogen, halogen, $C_1$-$C_4$-alkyl or $C_1$-$C_4$-haloalkyl having 1 to 5 halogen atoms.

DETAILED DESCRIPTION OF A PREFERRED EMBODIMENT

Furthermore, it has been found that biphenylcarboxamides of the formula (I) are obtained when
(a) carbonyl halides of the formula (II)

(II)

in which

A is as defined above, $X^1$ represents halogen or hydroxyl, are reacted with amines of the formula (III)

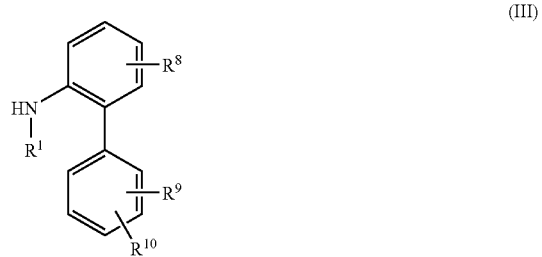

(III)

in which $R^1$, $R^8$, $R^9$ and $R^{10}$ are as defined above, if appropriate in the presence of a coupling agent, if appropriate in the presence of an acid binder and if appropriate in the presence of a diluent, or (b) biphenylcarboxamides of the formula (I-a)

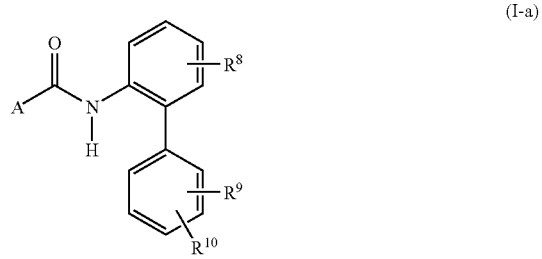

(I-a)

in which $R^8$, $R^9$, $R^{10}$ and A are as defined above are reacted with halides of the formula (IV)

$R^{1-B}$-Hal (IV)

in which $R^{1-B}$ represents $C_1$-$C_8$-alkyl, $C_1$-$C_6$-alkylsulphinyl, $C_1$-$C_6$-alkylsulphonyl, $C_1$-$C_4$-alkoxy-$C_1$-$C_4$-alkyl, $C_3$-$C_8$-cycloalkyl; $C_1$-$C_6$-haloalkyl, $C_1$-$C_4$-haloalkylthio, $C_1$-$C_4$-haloalkyl-sulphinyl, $C_1$-$C_4$-haloalkylsulphonyl, halogen-$C_1$-$C_4$-alkoxy-$C_1$-$C_4$-alkyl, $C_3$-$C_8$-halocycloalkyl having in each case 1 to 9 fluorine, chlorine and/or bromine atoms, formyl, formyl-$C_1$-$C_3$-alkyl, ($C_1$-$C_3$-alkyl)carbonyl-$C_1$-$C_3$-alkyl, ($C_1$-$C_3$-alkoxy)-carbonyl-$C_1$-$C_3$-alkyl; halo-($C_1$-$C_3$-alkyl)carbonyl-$C_1$-$C_3$-alkyl, halo-($C_1$-$C_3$-alkoxy)-carbonyl-$C_1$-$C_3$-alkyl having in each case 1 to 13 fluorine, chlorine and/or bromine atoms;

($C_1$-$C_8$-alkyl)carbonyl, ($C_1$-$C_8$-alkoxy)carbonyl, ($C_1$-$C_8$-alkylthio)carbonyl, ($C_1$-$C_4$-alkoxy-$C_1$-$C_4$-alkyl)carbonyl, ($C_3$-$C_6$-alkenyloxy)carbonyl, ($C_3$-$C_6$-alkynyloxy)-carbonyl, ($C_3$-$C_8$-cycloalkyl)carbonyl; ($C_1$-$C_6$-haloalkyl)carbonyl, ($C_1$-$C_6$-haloalkoxy)carbonyl, ($C_1$-$C_6$-haloalkylthio)carbonyl, (halo-$C_1$-$C_4$-alkoxy-$C_1$-$C_4$-alkyl)carbonyl, ($C_3$-$C_6$-haloalkenyloxy)carbonyl, ($C_3$-$C_6$-haloalkynyloxy)carbonyl, ($C_3$-$C_8$-halocycloalkyl)carbonyl having in each case 1 to 9 fluorine, chlorine and/or bromine atoms; or —$CH_2$—C≡C—$R^{1-A}$, —$CH_2$—CH=CH—$R^{1-A}$, —CH=C=CH—$R^{1-A}$, —C(=O)C(=O)$R^2$, —CONR$^3$R$^4$ or —$CH_2$NR$^5$R$^6$, $R^{1-A}$, $R^2$, $R^3$, $R^4$, $R^5$ and $R^6$ are as defined above,
Hal represents chlorine, bromine or iodine
in the presence of a base and in the presence of a diluent.

Finally, it has been found that the novel biphenylcarboxamides of the formula (I) have very good microbicidal properties and can be used for controlling unwanted microorganisms both in crop protection and in the protection of materials.

If appropriate, the compounds according to the invention can be present as mixtures of different possible isomeric forms, in particular of stereoisomers, such as, for example, E and Z, threo and erythro, and also optical isomers, and, if appropriate, also of tautomers. What is claimed are both the E and the Z isomers, and also the threo and erythro, and the optical isomers, any mixtures of these isomers, and the possible tautomeric forms.

The formula (I) provides a general definition of the biphenylcarboxamides according to the invention. Preferred radical definitions of the formulae mentioned above and below are stated below. These definitions apply to the end products of the formula (I) and likewise to all intermediates.

$R^1$ preferably represents hydrogen, $C_1$-$C_6$-alkyl, $C_1$-$C_4$-alkylsulphinyl, $C_1$-$C_4$-alkylsulphonyl, $C_1$-$C_3$-alkoxy-$C_1$-$C_3$-alkyl, $C_3$-$C_6$-cycloalkyl; $C_1$-$C_4$-haloalkyl, $C_1$-$C_4$-haloalkylthio, $C_1$-$C_4$-haloalkylsulphinyl, $C_1$-$C_4$-haloalkylsulphonyl, halo-$C_1$-$C_3$-alkoxy-$C_1$-$C_3$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$-alkyl)carbonyl-$C_1$-$C_3$-alkyl, halo-($C_1$-$C_3$-alkoxy)carbonyl-$C_1$-$C_3$-alkyl having in each case 1 to 13 fluorine, chlorine and/or bromine atoms;

($C_1$-$C_6$-alkyl)carbonyl, ($C_1$-$C_4$-alkoxy)carbonyl, ($C_1$-$C_4$-alkylthio)carbonyl, ($C_1$-$C_3$-alkoxy-$C_1$-$C_3$-alkyl)carbonyl, ($C_3$-$C_4$-alkenyloxy)carbonyl, ($C_3$-$C_4$-alkynyloxy)carbonyl, ($C_3$-$C_6$-cycloalkyl)carbonyl; ($C_1$-$C_4$-haloalkyl)carbonyl, ($C_1$-$C_4$-haloalkoxy)carbonyl, ($C_1$-$C_4$-haloalkylthio)carbonyl, (halo-$C_1$-$C_3$-alkoxy-$C_1$-$C_3$-alkyl)carbonyl, ($C_3$-$C_4$-haloalkenyloxy)-carbonyl, ($C_3$-$C_4$-haloalkynyloxy)carbonyl, ($C_3$-$C_6$-halocycloalkyl)carbonyl having in each case 1 to 9 fluorine, chlorine and/or bromine atoms; or —$CH_2$—C≡C—$R^{1-A}$, —$CH_2$—CH=CH—$R^{1-A}$, —CH=C=CH—$R^{1-A}$, —C(=O)C(=O)$R^2$, —CONR$^3$R$^4$ or —$CH_2$NR$^5$R$^6$.

$R^1$ particularly preferably represents hydrogen, methyl, ethyl, n- or isopropyl, n-, iso-, sec- or tert-butyl, pentyl or hexyl; methylsulphinyl, ethylsulphinyl, n- or isopropylsulphinyl, n-, iso-, sec- or tert-butylsulphinyl, methylsulphonyl, ethylsulphonyl, n- or isopropylsulphonyl, n-, iso-, sec- or tert-butylsulphonyl, methoxymethyl, methoxyethyl, ethoxymethyl, ethoxyethyl, cyclopropyl, cyclopentyl, cyclohexyl, trifluoromethyl, trichloromethyl, trifluoroethyl, difluoromethylthio, difluorochloromethylthio, trifluoromethylthio, trifluoromethylsulphinyl, trifluoromethyl-sulphonyl, trifluoromethoxymethyl; formyl, —$CH_2$—CHO, —$(CH_2)_2$—CHO, —$CH_2$—CO—$CH_3$, —$CH_2$—CO—$CH_2CH_3$, —$CH_2$—CO—CH($CH_3$)$_2$, —$(CH_2)_2$—CO—$CH_3$, —$(CH_2)_2$—CO—$CH_2CH_3$, —$(CH_2)_2$—CO—CH($CH_3$)$_2$, —$CH_2$—$CO_2CH_3$, —$CH_2$—$CO_2CH_2CH_3$, —$CH_2$—$CO_2$CH($CH_3$)$_2$, —$(CH_2)_2$—$CO_2CH_3$, —$(CH_2)_2$—$CO_2CH_2CH_3$, —$(CH_2)_2$—$CO_2$CH($CH_3$)$_2$, —$CH_2$—CO—$CF_3$, —$CH_2$—CO—$CCl_3$, —$CH_2$—CO—$CH_2CF_3$, —$CH_2$—CO—$CH_2CCl_3$, —$(CH_2)_2CO$—$CH_2CF_3$, —$(CH_2)_2$—CO—$CH_2CCl_3$, —$CH_2$—$CO_2CH_2CF_3$, —$CH_2$—$CO_2CF_2CF_3$, —$CH_2$—$CO_2CH_2CCl_3$, —$CH_2$—$CO_2CCl_2CCl_3$, —$(CH_2)_2$—$CO_2CH_2CF_3$, —$(CH_2)_2$—$CO_2CF_2CF_3$, —$(CH_2)_2$—$CO_2CH_2CCl_3$, —$(CH_2)_2$—$CO_2CCl_2CCl_3$; methylcarbonyl, ethylcarbonyl, n-propylcarbonyl, isopropylcarbonyl, tert-butylcarbonyl, methoxycarbonyl, ethoxycarbonyl, isopropoxycarbonyl, tert-butoxycarbonyl, methyl-thiocarbonyl, ethylthiocarbonyl, isopropylthiocarbonyl, tert-butylthiocarbonyl, methoxymethylcarbonyl, ethoxymethylcarbonyl, cyclopropylcarbonyl; trifluoromethyl-carbonyl, trifluoromethoxycarbonyl, trifluoromethylthiocarbonyl, or —$CH_2$—C≡C—$R^{1-A}$, —$CH_2$—CH=CH—$R^{1-A}$, —CH=C=CH—$R^{1-A}$, —C(=O)C(=O)$R^2$, —CONR$^3$R$^4$ or —$CH_2$NR$^5$R$^6$.

$R^1$ very particularly preferably represents hydrogen, methyl, methoxymethyl, methoxymethylcarbonyl, ethoxymethylcarbonyl, formyl, —$CH_2$—C≡CH, —$CH_2$—CH=$CH_2$, —CH=C=$CH_2$, —$CH_2$—CHO, —$(CH_2)_2$—CHO, —$CH_2$—CO—$CH_3$, —$CH_2$—CO—$CH_2CH_3$, —$CH_2$—CO—CH($CH_3$)$_2$ —C(=O)CHO, —C(=O)C(=O)$CH_3$, —C(=O)C(=O)$CH_2OCH_3$, —C(=O)$CO_2CH_3$, —C(=O)$CO_2CH_2CH_3$.

$R^{1-A}$ preferably represents hydrogen, $C_1$-$C_4$-alkyl, $C_1$-$C_4$-haloalkyl, $C_2$-$C_4$-alkenyl, $C_2$-$C_4$-alkynyl, $C_3$-$C_6$-cycloalkyl, ($C_1$-$C_4$-alkoxy)carbonyl, or cyano.

$R^{1-A}$ particularly preferably represents hydrogen, methyl or ethyl.

$R^2$ preferably represents hydrogen, $C_1$-$C_6$-alkyl, $C_1$-$C_4$-alkoxy, $C_1$-$C_3$-alkoxy-$C_1$-$C_3$-alkyl, $C_3$-$C_6$-cycloalkyl; $C_1$-$C_4$-haloalkyl, $C_1$-$C_4$-haloalkoxy, halo-$C_1$-$C_3$-alkoxy-$C_1$-$C_3$-alkyl, $C_3$-$C_6$-halocycloalkyl having in each case 1 to 9 fluorine, chlorine and/or bromine atoms.

$R^2$ particularly preferably represents hydrogen, methyl, ethyl, n- or isopropyl, tert-butyl, methoxy, ethoxy, n- or isopropoxy, tert-butoxy, methoxymethyl, cyclopropyl; trifluoromethyl, trifluoromethoxy.

$R^3$ and $R^4$ independently of one another preferably represent hydrogen, $C_1$-$C_6$-alkyl, $C_1$-$C_3$-alkoxy-$C_1$-$C_3$-alkyl, $C_3$-$C_6$-cycloalkyl; $C_1$-$C_4$-haloalkyl, halo-$C_1$-$C_3$-alkoxy-$C_1$-$C_3$-alkyl, $C_3$-$C_6$-halocycloalkyl having in each case 1 to 9 fluorine, chlorine and/or bromine atoms.

$R^3$ and $R^4$ furthermore together with the nitrogen atom to which they are attached preferably form a saturated heterocycle which is optionally mono- to tetrasubstituted by identical or different substituents from the group consisting of halogen and $C_1$-$C_4$-alkyl and which has 5 or 6 ring atoms, where the heterocycle may contain 1 or 2 further non-adjacent heteroatoms from the group consisting of oxygen, sulphur and NR$^7$.

$R^3$ and $R^4$ independently of one another particularly preferably represent hydrogen, methyl, ethyl, n- or isopropyl, n-, iso-, sec- or tert-butyl, methoxymethyl, methoxyethyl, ethoxymethyl, ethoxyethyl, cyclopropyl, cyclopentyl, cyclohexyl; trifluoromethyl, trichloromethyl, trifluoroethyl, trifluoromethoxymethyl.

$R^3$ and $R^4$ furthermore together with the nitrogen atom to which they are attached particularly preferably form a saturated heterocycle from the group consisting of morpholine, thiomorpholine and piperazine which is optionally mono- to tetrasubstituted by identical or different substituents from the group consisting of fluorine, chlorine, bromine and methyl, where the piperazine may be substituted on the second nitrogen atom by $R^7$.

$R^5$ and $R^6$ independently of one another preferably represent hydrogen, $C_1$-$C_6$-alkyl, $C_3$-$C_6$-cycloalkyl; $C_1$-$C_4$-haloalkyl, $C_3$-$C_6$-halocycloalkyl having in each case 1 to 9 fluorine, chlorine and/or bromine atoms.

$R^5$ and $R^6$ furthermore together with the nitrogen atom to which they are attached preferably form a saturated heterocycle which is optionally mono- or polysubstituted by identical or different substituents from the group consisting of halogen and $C_1$-$C_4$-alkyl and which has 5 or 6 ring atoms, where the heterocycle may contain 1 or 2 further non-adjacent heteroatoms from the group consisting of oxygen, sulphur and $NR^7$.

$R^5$ and $R^6$ independently of one another particularly preferably represent hydrogen, methyl, ethyl, n- or isopropyl, n-, iso-, sec- or tert-butyl, methoxymethyl, methoxyethyl, ethoxymethyl, ethoxyethyl, cyclopropyl, cyclopentyl, cyclohexyl; trifluoromethyl, trichloromethyl, trifluoroethyl, trifluoromethoxymethyl.

$R^5$ and $R^6$ furthermore together with the nitrogen atom to which they are attached particularly preferably form a saturated heterocycle from the group consisting of morpholine, thiomorpholine and piperazine which is optionally mono- to tetrasubstituted by identical or different substituents from the group consisting of fluorine, chlorine, bromine and methyl, where the piperazine may be substituted on the second nitrogen atom by $R^7$.

$R^7$ preferably represents hydrogen or $C_1$-$C_4$-alkyl.

$R^7$ particularly preferably represents hydrogen, methyl, ethyl, n- or isopropyl, n-, iso-, sec- or tert-butyl.

$R^8$ preferably represents hydrogen.

$R^8$ particularly preferably represents fluorine.

$R^9$ preferably represents —$SO_mR^{11}$.

$R^9$ furthermore preferably represents —$SO_2NR^{12}R^{13}$.

$R^9$ furthermore preferably represents —$C(=X)R^{14}$.

$R^9$ furthermore preferably represents —$Si(R^{15})_3$.

$R^9$ furthermore preferably represents —$NR^{12}R^{13}$.

$R^9$ furthermore preferably represents —$CH_2$—$NR^{12}R^{13}$.

$R^{10}$ preferably represents fluorine, chlorine or bromine.

$R^{10}$ furthermore preferably represents methyl or trifluoromethyl.

$R^{10}$ particularly preferably represents fluorine.

$R^{10}$ furthermore particularly preferably represents chlorine.

$R^{10}$ furthermore particularly preferably represents methyl.

$R^{10}$ furthermore particularly preferably represents trifluoromethyl.

$R^{11}$ preferably represents $C_1$-$C_4$-alkyl or $C_1$-$C_4$-haloalkyl having 1 to 9 fluorine, chlorine and/or bromine atoms.

$R^{11}$ particularly preferably represents methyl, ethyl, n-, isopropyl, n-, i-, s-, t-butyl, trifluoromethyl, —$CH_2CF_3$, —$C_2F_5$ or trichloromethyl.

$R^{11}$ very particularly preferably represents methyl, trifluoromethyl, —$CH_2CF_3$ or —$C_2F_5$.

m preferably represents 1.

m also preferably represents 2.

m particularly preferably represents 2.

$R^{12}$ preferably represents hydrogen, methyl, ethyl, n- or isopropyl, n-, iso-, sec- or tert-butyl or —$C(=X)R^{14}$.

$R^{12}$ particularly preferably represents hydrogen, methyl, ethyl, n- or isopropyl or —$C(=X)R^{14}$.

$R^{12}$ very particularly preferably represents hydrogen or methyl.

$R^{13}$ preferably represents hydrogen, methyl, ethyl, n- or isopropyl, n-, iso-, sec- or tert-butyl or —$C(=X)R^{14}$.

$R^{13}$ particularly preferably represents hydrogen, methyl, ethyl, n- or isopropyl or —$C(=X)R^{14}$.

$R^{13}$ very particularly preferably represents hydrogen or methyl.

$R^{12}$ and $R^{13}$ furthermore together with the nitrogen atom to which they are attached preferably form a saturated heterocycle which is optionally mono- or polysubstituted by identical or different substituents from the group consisting of halogen and $C_1$-$C_4$-alkyl and has 5 or 6 ring atoms, where the heterocycle may contain 1 or 2 further non-adjacent heteroatoms from the group consisting of oxygen, sulphur and $NR^7$.

$R^{12}$ and $R^{13}$ furthermore together with the nitrogen atom to which they are attached particularly preferably form a saturated heterocycle from the group consisting of morpholine, thiomorpholine and piperazine which is optionally mono- to tetrasubstituted by identical or different substituents from the group consisting of fluorine, chlorine, bromine and methyl, where the piperazine may be substituted on the second nitrogen atom by $R^7$.

X preferably represents O (oxygen).

X also preferably represents S (sulphur).

$R^{14}$ preferably represents hydrogen, methyl, ethyl, n- or isopropyl, n-, iso-, sec- or tert-butyl, methoxy, ethoxy, n- or isopropoxy, n-, iso-, sec- or tert-butoxy or —$NR^{16}R^{17}$.

$R^{14}$ particularly preferably represents hydrogen, methyl, ethyl, n- or isopropyl, methoxy, ethoxy, n- or isopropoxy or —$NR^{16}R^{17}$.

$R^{14}$ very particularly preferably represents hydrogen, methyl, ethyl, methoxy, ethoxy or —$NR^{16}R^{17}$.

$R^{15}$ preferably represents $C_1$-$C_6$-alkyl, $C_1$-$C_6$-alkoxy, $C_1$-$C_3$-alkoxy-$C_1$-$C_3$-alkyl or $C_1$-$C_3$-alkylthio-$C_1$-$C_3$-alkyl, where the three radicals $R^{15}$ may each be identical or different.

$R^{15}$ particularly preferably represents methyl, ethyl, methoxy, ethoxy, methoxymethyl, ethoxymethyl, methoxyethyl, ethoxyethyl, methylthiomethyl, ethylthiomethyl, methylthioethyl or ethylthioethyl, where the three radicals $R^{15}$ may each be identical or different.

$R^{15}$ very particularly preferably represents methyl, methoxy, methoxymethyl or methylthio-methyl, where the three radicals $R^{15}$ may each be identical or different.

$R^{15}$ especially represents methyl.

$R^{16}$ preferably represents hydrogen, methyl, ethyl, n- or isopropyl, n-, iso-, sec- or tert-butyl.

$R^{16}$ particularly preferably represents hydrogen, methyl, ethyl, n- or isopropyl.

$R^{16}$ very particularly preferably represents hydrogen or methyl.

$R^{17}$ preferably represents hydrogen, methyl, ethyl, n- or isopropyl, n-, iso-, sec- or tert-butyl.

$R^{17}$ particularly preferably represents hydrogen, methyl, ethyl, n- or isopropyl.

$R^{17}$ very particularly preferably represents hydrogen or methyl.

$R^{16}$ and $R^{17}$ furthermore together with the nitrogen atom to which they are attached preferably form a saturated heterocycle which is optionally mono- or polysubstituted by identical or different substituents from the group consisting of halogen and $C_1$-$C_4$-alkyl and has 5 or 6 ring atoms, where the heterocycle may contain 1 or 2 further non-adjacent heteroatoms from the group consisting of oxygen, sulphur and $NR^7$.

$R^{16}$ and $R^{17}$ furthermore together with the nitrogen atom to which they are attached particularly preferably form a saturated heterocycle from the group consisting of morpholine, thiomorpholine and piperazine which is optionally mono- to tetrasubstituted by identical or different substituents from the group consisting of fluorine, chlorine, bromine and methyl, where the piperazine may be substituted on the second nitrogen atom by $R^7$.

A preferably represents one of the radicals A1, A2, A3, A4, A5, A6, A9, A10, A11, A12 or A17.

A particularly preferably represents one of the radicals A1, A2, A4, A5, A6, A9, A11, A16, A17.

A very particularly preferably represents the radical A1.

A furthermore very particularly preferably represents the radical A2.

A furthermore very particularly preferably represents the radical A4.

A furthermore very particularly preferably represents the radical A5.

A furthermore very particularly preferably represents the radical A6.

A furthermore very particularly preferably represents the radical A9.

A furthermore very particularly preferably represents the radical A11.

A furthermore very particularly preferably represents the radical A16.

A furthermore very particularly preferably represents the radical A17.

$R^{18}$ preferably represents hydrogen, cyano, fluorine, chlorine, bromine, iodine, methyl, ethyl, isopropyl, methoxy, ethoxy, methylthio, ethylthio, cyclopropyl, $C_1$-$C_2$-haloalkyl, $C_1$-$C_2$-haloalkoxy having in each case 1 to 5 fluorine, chlorine and/or bromine atoms, trifluoro-methylthio, difluoromethylthio, aminocarbonyl, aminocarbonylmethyl or aminocarbonyl-ethyl.

$R^{18}$ particularly preferably represents hydrogen, fluorine, chlorine, bromine, iodine, methyl, ethyl, isopropyl, monofluoromethyl, monofluoroethyl, difluoromethyl, trifluoromethyl, difluorochloromethyl, trichloromethyl, dichloromethyl, cyclopropyl, methoxy, ethoxy, trifluoromethoxy, trichloromethoxy, methylthio, ethylthio, trifluoromethylthio or difluoromethylthio.

$R^{18}$ very particularly preferably represents hydrogen, fluorine, chlorine, bromine, iodine, methyl, isopropyl, monofluoromethyl, monofluoroethyl, difluoromethyl, trifluoromethyl, difluoro-chloromethyl or trichloromethyl.

$R^{18}$ especially preferably represents methyl, difluoromethyl, trifluoromethyl or 1-fluoroethyl.

$R^{19}$ preferably represents hydrogen, fluorine, chlorine, bromine, iodine, methyl, ethyl, methoxy, ethoxy, methylthio or ethylthio.

$R^{19}$ particularly preferably represents hydrogen, fluorine, chlorine, bromine, iodine or methyl.

$R^{19}$ very particularly preferably represents hydrogen, fluorine, chlorine or methyl.

$R^{20}$ preferably represents hydrogen, methyl, ethyl, n-propyl, isopropyl, $C_1$-$C_2$-haloalkyl having 1 to 5 fluorine, chlorine and/or bromine atoms, hydroxymethyl, hydroxyethyl, cyclopropyl, cyclopentyl, cyclohexyl or phenyl.

$R^{20}$ particularly preferably represents hydrogen, methyl, ethyl, isopropyl, trifluoromethyl, difluoromethyl, hydroxymethyl, hydroxyethyl or phenyl.

$R^{20}$ very particularly preferably represents hydrogen, methyl, trifluoromethyl or phenyl.

$R^{20}$ especially preferably represents methyl.

$R^{21}$ and $R^{22}$ independently of one another preferably represent hydrogen, fluorine, chlorine, bromine, methyl, ethyl or $C_1$-$C_2$-haloalkyl having 1 to 5 fluorine, chlorine and/or bromine atoms.

$R^{21}$ and $R^{22}$ independently of one another particularly preferably represent hydrogen, fluorine, chlorine, bromine, methyl, ethyl, difluoromethyl, trifluoromethyl, difluorochloromethyl or trichloromethyl.

$R^{21}$ and $R^{22}$ independently of one another very particularly preferably represent hydrogen, fluorine, chlorine, bromine, methyl, ethyl, difluoromethyl, trifluoromethyl or trichloromethyl.

$R^{21}$ and $R^{22}$ preferably each represent hydrogen.

$R^{23}$ preferably represents fluorine, chlorine, bromine, cyano, methyl, ethyl, $C_1$-$C_2$-haloalkyl or $C_1$-$C_2$-haloalkoxy having in each case 1 to 5 fluorine, chlorine and/or bromine atoms.

$R^{23}$ particularly preferably represents fluorine, chlorine, bromine, cyano, methyl, trifluoromethyl, trifluoromethoxy, difluoromethoxy, difluorochloromethoxy or trichloromethoxy.

$R^{23}$ very particularly preferably represents fluorine, chlorine, bromine, iodine, methyl, trifluoromethyl or trifluoromethoxy.

$R^{23}$ especially preferably represents methyl or trifluoromethyl.

$R^{24}$ and $R^{25}$ independently of one another preferably represent hydrogen, fluorine, chlorine, bromine, methyl, ethyl or $C_1$-$C_2$-haloalkyl having 1 to 5 fluorine, chlorine and/or bromine atoms.

$R^{24}$ and $R^{25}$ independently of one another particularly preferably represent hydrogen, fluorine, chlorine, bromine, methyl, ethyl, difluoromethyl, trifluoromethyl, difluorochloromethyl or trichloromethyl.

$R^{24}$ and $R^{25}$ independently of one another very particularly preferably represent hydrogen, fluorine, chlorine, bromine, methyl, ethyl, difluoromethyl, trifluoromethyl or trichloromethyl.

$R^{24}$ and $R^{25}$ especially preferably each represent hydrogen.

$R^{26}$ preferably represents hydrogen, fluorine, chlorine, bromine, iodine, methyl, ethyl or $C_1$-$C_2$-haloalkyl having 1 to 5 fluorine, chlorine and/or bromine atoms.

$R^{26}$ particularly preferably represents hydrogen, fluorine, chlorine, bromine, iodine, methyl or trifluoromethyl.

$R^{26}$ very particularly preferably represents fluorine, chlorine, bromine, iodine, methyl or trifluoromethyl.

$R^{27}$ preferably represents hydrogen, fluorine, chlorine, bromine, iodine, hydroxyl, cyano, $C_1$-$C_4$-alkyl, $C_1$-$C_2$-haloalkyl, $C_1$-$C_2$-haloalkoxy or $C_1$-$C_2$-haloalkylthio having in each case 1 to 5 fluorine, chlorine and/or bromine atoms.

$R^{27}$ particularly preferably represents hydrogen, fluorine, chlorine, bromine, iodine, hydroxyl, cyano, methyl, ethyl, n-propyl, isopropyl, n-butyl, isobutyl, sec-butyl, tert-butyl, difluoromethyl, trifluoromethyl, difluorochloromethyl, trichloromethyl, trifluoromethoxy, difluoromethoxy, difluorochloromethoxy, trichloromethoxy, trifluoromethylthio, difluoromethylthio, difluoro-chloromethylthio or trichloromethylthio.

$R^{27}$ very particularly preferably represents hydrogen, fluorine, chlorine, bromine, iodine, methyl, difluoromethyl, trifluoromethyl or trichloromethyl.

$R^{27}$ especially preferably represents iodine, methyl, difluoromethyl or trifluoromethyl.

$R^{28}$ preferably represents fluorine, chlorine, bromine, iodine, hydroxyl, cyano, $C_1$-$C_4$-alkyl, methoxy, ethoxy, methylthio, ethylthio, difluoromethylthio, trifluoromethylthio, $C_1$-$C_2$-haloalkyl or $C_1$-$C_2$-haloalkoxy having in each case 1 to 5 fluorine, chlorine and/or bromine atoms.

$R^{28}$ particularly preferably represents fluorine, chlorine, bromine, iodine, hydroxyl, cyano, methyl, ethyl, n-propyl, isopropyl, n-butyl, isobutyl, sec-butyl, tert-butyl, trifluoromethyl, difluoromethyl, difluorochloromethyl, trichloromethyl, methoxy, ethoxy, methylthio, ethylthio, difluoromethylthio, trifluoromethylthio, trifluoromethoxy, difluoromethoxy, difluorochloromethoxy or trichloromethoxy.

$R^{28}$ very particularly preferably represents fluorine, chlorine, bromine, iodine, methyl, trifluoromethyl, difluoromethyl or trichloromethyl.

$R^{29}$ preferably represents hydrogen, fluorine, chlorine, bromine, iodine, cyano, $C_1$-$C_4$-alkyl, methoxy, ethoxy, methylthio, ethylthio, $C_1$-$C_2$-haloalkyl or $C_1$-$C_2$-haloalkoxy having in each case 1 to 5 fluorine, chlorine and/or bromine atoms, $C_1$-$C_2$-alkylsulphinyl or $C_1$-$C_2$-alkylsulphonyl.

$R^{29}$ particularly preferably represents hydrogen, fluorine, chlorine, bromine, iodine, cyano, n-propyl, isopropyl, n-butyl, isobutyl, sec-butyl, tert-butyl, trifluoromethyl, difluoromethyl, difluorochloromethyl, trichloromethyl, methoxy, ethoxy, methylthio, ethylthio, trifluoromethoxy, difluoromethoxy, difluorochloromethoxy, trichloromethoxy, methylsulphinyl or methylsulphonyl.

$R^{29}$ very particularly preferably represents hydrogen, fluorine, chlorine, bromine, iodine, n-propyl, isopropyl, n-butyl, isobutyl, sec-butyl, tert-butyl, trifluoromethyl, difluoromethyl, trichloromethyl, methylsulphinyl or methylsulphonyl.

$R^{29}$ especially preferably represents hydrogen.

$R^{30}$ preferably represents methyl, ethyl or $C_1$-$C_2$-haloalkyl having 1 to 5 fluorine, chlorine and/or bromine atoms.

$R^{30}$ particularly preferably represents methyl, ethyl, trifluoromethyl, difluoromethyl, difluorochloromethyl or trichloromethyl.

$R^{31}$ preferably represents methyl or ethyl.

$R^{31}$ particularly preferably represents methyl.

$Q^1$ preferably represents S (sulphur), $SO_2$ or $CH_2$.

$Q^1$ particularly preferably represents S (sulphur) or $CH_2$.

$Q^1$ very particularly preferably represents S (sulphur).

p preferably represents 0 or 1.

p particularly preferably represents 0.

$R^{32}$ preferably represents methyl, ethyl or $C_1$-$C_2$-haloalkyl having 1 to 5 fluorine, chlorine and/or bromine atoms.

$R^{32}$ particularly preferably represents methyl, ethyl, trifluoromethyl, difluoromethyl, difluoro-chloromethyl or trichloromethyl.

$R^{32}$ very particularly preferably represents methyl, trifluoromethyl, difluoromethyl or trichloromethyl.

$R^{33}$ preferably represents methyl, ethyl or $C_1$-$C_2$-haloalkyl having 1 to 5 fluorine, chlorine and/or bromine atoms.

$R^{33}$ particularly preferably represents methyl, ethyl, trifluoromethyl, difluoromethyl, difluorochloromethyl or trichloromethyl.

$R^{33}$ very particularly preferably represents methyl, trifluoromethyl, difluoromethyl or trichloromethyl.

$R^{34}$ and $R^{35}$ independently of one another preferably represents hydrogen, fluorine, chlorine, bromine, amino, methyl, ethyl or $C_1$-$C_2$-haloalkyl having 1 to 5 fluorine, chlorine and/or bromine atoms.

$R^{34}$ and $R^{35}$ independently of one another particularly preferably represent hydrogen, fluorine, chlorine, bromine, methyl, ethyl, trifluoromethyl, difluoromethyl, difluorochloromethyl or trichloromethyl.

$R^{34}$ and $R^{35}$ independently of one another very particularly preferably represent hydrogen, fluorine, chlorine, bromine, methyl, trifluoromethyl, difluoromethyl or trichloromethyl.

$R^{34}$ and $R^{35}$ especially preferably each represent hydrogen.

$R^{36}$ preferably represents hydrogen, fluorine, chlorine, bromine, iodine, methyl, ethyl or $C_1$-$C_2$-haloalkyl having 1 to 5 fluorine, chlorine and/or bromine atoms.

$R^{36}$ particularly preferably represents hydrogen, fluorine, chlorine, bromine, iodine, methyl, ethyl, trifluoromethyl, difluoromethyl, difluorochloromethyl or trichloromethyl.

$R^{36}$ very particularly preferably represents hydrogen, fluorine, chlorine, bromine, iodine, methyl, trifluoromethyl, difluoromethyl or trichloromethyl.

$R^{36}$ especially preferably represents methyl.

$R^{37}$ and $R^{38}$ independently of one another preferably represent hydrogen, fluorine, chlorine, bromine, amino, nitro, methyl, ethyl or $C_1$-$C_2$-haloalkyl having 1 to 5 fluorine, chlorine and/or bromine atoms.

$R^{37}$ and $R^{38}$ independently of one another particularly preferably represent hydrogen, fluorine, chlorine, bromine, nitro, methyl, ethyl, trifluoromethyl, difluoromethyl, difluorochloromethyl or trichloromethyl.

$R^{37}$ and $R^{38}$ independently of one another very particularly preferably represent hydrogen, fluorine, chlorine, bromine, methyl, trifluoromethyl, difluoromethyl or trichloromethyl.

$R^{37}$ and $R^{38}$ especially preferably each represent hydrogen.

$R^{39}$ preferably represents hydrogen, fluorine, chlorine, bromine, methyl, ethyl or $C_1$-$C_2$-haloalkyl having 1 to 5 fluorine, chlorine and/or bromine atoms.

$R^{39}$ particularly preferably represents hydrogen, fluorine, chlorine, bromine, methyl, ethyl, trifluoromethyl, difluoromethyl, difluorochloromethyl or trichloromethyl.

$R^{39}$ very particularly preferably represents hydrogen, fluorine, chlorine, bromine, methyl, trifluoromethyl, difluoromethyl or trichloromethyl.

$R^{39}$ represents methyl.

$R^{40}$ preferably represents hydrogen, fluorine, chlorine, bromine, amino, $C_1$-$C_4$-alkylamino, di($C_1$-$C_4$-alkyl)amino, cyano, methyl, ethyl or $C_1$-$C_2$-haloalkyl having 1 to 5 fluorine, chlorine and/or bromine atoms.

$R^{40}$ particularly preferably represents hydrogen, fluorine, chlorine, bromine, amino, methyl-amino, dimethylamino, cyano, methyl, ethyl, trifluoromethyl, difluoromethyl, difluorochloromethyl or trichloromethyl.

$R^{40}$ very particularly preferably represents hydrogen, fluorine, chlorine, bromine, amino, methylamino, dimethylamino, methyl, trifluoromethyl, difluoromethyl or trichloromethyl.

$R^{40}$ especially preferably represents amino, methylamino, dimethylamino, methyl or trifluoromethyl.

$R^{41}$ preferably represents fluorine, chlorine, bromine, methyl, ethyl or $C_1$-$C_2$-haloalkyl having 1 to 5 fluorine, chlorine and/or bromine atoms.

$R^{41}$ particularly preferably represents fluorine, chlorine, bromine, methyl, ethyl, trifluoromethyl, difluoromethyl, difluorochloromethyl or trichloromethyl.

$R^{41}$ very particularly preferably represents fluorine, chlorine, bromine, methyl, trifluoromethyl, difluoromethyl or trichloromethyl.

$R^{41}$ especially preferably represents methyl, trifluoromethyl or difluoromethyl.

$R^{42}$ preferably represents hydrogen, fluorine, chlorine, bromine, amino, $C_1$-$C_4$-alkylamino, di($C_1$-$C_4$-alkyl)amino, cyano, methyl, ethyl or $C_1$-$C_2$-haloalkyl having 1 to 5 fluorine, chlorine and/or bromine atoms.

$R^{42}$ particularly preferably represents hydrogen, fluorine, chlorine, bromine, amino, methyl-amino, dimethylamino, cyano, methyl, ethyl, trifluoromethyl, difluoromethyl, difluorochloromethyl or trichloromethyl.

$R^{42}$ very particularly preferably represents hydrogen, fluorine, chlorine, bromine, amino, methyl-amino, dimethylamino, methyl, trifluoromethyl, difluoromethyl or trichloromethyl.

$R^{42}$ especially preferably represents amino, methylamino, dimethylamino, methyl or trifluoromethyl.

$R^{43}$ preferably represents fluorine, chlorine, bromine, methyl, ethyl or $C_1$-$C_2$-haloalkyl having 1 to 5 fluorine, chlorine and/or bromine atoms.

$R^{43}$ particularly preferably represents fluorine, chlorine, bromine, methyl, ethyl, trifluoromethyl, difluoromethyl, difluorochloromethyl or trichloromethyl.

$R^{43}$ very particularly preferably represents fluorine, chlorine, bromine, methyl, trifluoromethyl, difluoromethyl or trichloromethyl.

$R^{43}$ especially preferably represents methyl, trifluoromethyl or difluoromethyl.

$R^{44}$ preferably represents fluorine, chlorine, bromine, methyl, ethyl or $C_1$-$C_2$-haloalkyl having 1 to 5 fluorine, chlorine and/or bromine atoms.

$R^{44}$ particularly preferably represents fluorine, chlorine, bromine, methyl, ethyl, trifluoromethyl, difluoromethyl, difluorochloromethyl or trichloromethyl.

$R^{44}$ very particularly preferably represents fluorine, chlorine, bromine, methyl, trifluoromethyl, difluoromethyl or trichloromethyl.

$R^{45}$ preferably represents hydrogen, methyl or ethyl.

$R^{45}$ particularly preferably represents methyl.

$R^{46}$ preferably represents fluorine, chlorine, bromine, methyl or ethyl.

$R^{46}$ particularly preferably represents fluorine, chlorine or methyl.

$R^{47}$ preferably represents methyl, ethyl or $C_1$-$C_2$-haloalkyl having 1 to 5 fluorine, chlorine and/or bromine atoms.

$R^{47}$ particularly preferably represents methyl, ethyl, trifluoromethyl, difluoromethyl, difluorochloromethyl or trichloromethyl.

$R^{47}$ very particularly preferably represents methyl, trifluoromethyl, difluoromethyl or trichloromethyl.

$R^{47}$ especially represents methyl or trifluoromethyl.

$R^{48}$ preferably represents hydrogen, fluorine, chlorine, bromine, methyl, ethyl or $C_1$-$C_2$-haloalkyl having 1 to 5 fluorine, chlorine and/or bromine atoms.

$R^{48}$ particularly preferably represents hydrogen, fluorine, chlorine, bromine, methyl or trifluoromethyl.

$R^{49}$ preferably represents fluorine, chlorine, bromine, iodine, hydroxyl, $C_1$-$C_4$-alkyl, methoxy, ethoxy, methylthio, ethylthio, difluoromethylthio, trifluoromethylthio, $C_1$-$C_2$-haloalkyl or $C_1$-$C_2$-haloalkoxy having in each case 1 to 5 fluorine, chlorine and/or bromine atoms.

$R^{49}$ particularly preferably represents fluorine, chlorine, bromine, iodine, methyl, ethyl, n-propyl, isopropyl, n-butyl, isobutyl, sec-butyl, tert-butyl, trifluoromethyl, difluoromethyl, difluorochloromethyl or trichloromethyl.

$R^{49}$ very particularly preferably represents fluorine, chlorine, bromine, iodine, methyl, trifluoromethyl, difluoromethyl or trichloromethyl.

$R^{50}$ preferably represents methyl, ethyl, n-propyl or isopropyl.

$R^{50}$ particularly preferably represents methyl or ethyl.

$R^{51}$ preferably represents hydrogen, methyl, ethyl, $C_1$-$C_2$-haloalkyl having 1 to 5 fluorine, chlorine and/or bromine atoms, $C_1$-$C_2$-alkoxy-$C_1$-$C_2$-alkyl, hydroxymethyl, hydroxyethyl, methylsulphonyl or dimethylaminosulphonyl.

$R^{51}$ particularly preferably represents hydrogen, methyl, ethyl, trifluoromethyl, methoxymethyl, ethoxymethyl, hydroxymethyl or hydroxyethyl.

$R^{51}$ very particularly preferably represents methyl or methoxymethyl.

$R^{52}$ preferably represents hydrogen, fluorine, chlorine, bromine, methyl, ethyl or $C_1$-$C_2$-haloalkyl having 1 to 5 fluorine, chlorine and/or bromine atoms.

$R^{52}$ particularly preferably represents hydrogen, fluorine, chlorine, bromine, methyl, ethyl, trifluoromethyl, difluoromethyl or trichloromethyl.

$R^{52}$ very particularly preferably represents hydrogen or methyl.

$R^{53}$ preferably represents hydrogen, fluorine, chlorine, bromine, iodine, cyano, methyl, ethyl, isopropyl or $C_1$-$C_2$-haloalkyl having 1 to 5 fluorine, chlorine and/or bromine atoms.

$R^{53}$ particularly preferably represents hydrogen, fluorine, chlorine, bromine, cyano, methyl, ethyl, isopropyl, trifluoromethyl, difluoromethyl, difluorochloromethyl or trichloromethyl.

$R^{53}$ very particularly preferably represents hydrogen, methyl, difluoromethyl or trifluoromethyl.

$R^{54}$ preferably represents hydrogen, fluorine, chlorine, bromine, methyl, ethyl or $C_1$-$C_2$-haloalkyl having 1 to 5 fluorine, chlorine and/or bromine atoms.

$R^{54}$ particularly preferably represents hydrogen, fluorine, chlorine, bromine, iodine, methyl or trifluoromethyl.

$R^{54}$ very particularly preferably represents hydrogen.

Preference is given to those compounds of the formula (I) in which all radicals each have the preferred meanings mentioned above.

Particular preference is given to those compounds of the formula (I) in which all the radicals each have the particularly preferred meanings mentioned above.

Preference is furthermore given to compounds of the formula (I-b)

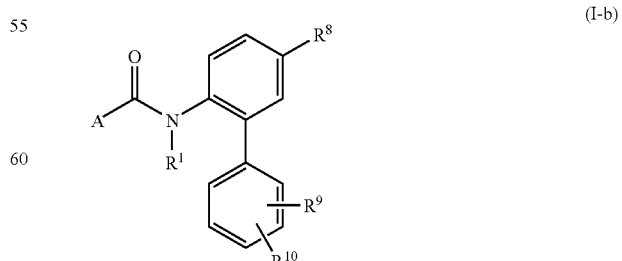

(I-b)

in which $R^1$, $R^8$, $R^9$, $R^{10}$ and A are as defined above.

Preference is furthermore given to compounds of the formula (I-c)

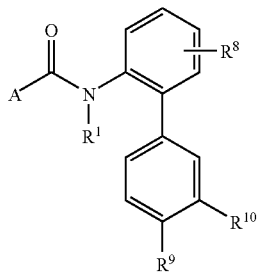

(I-c)

in which $R^1$, $R^8$, $R^9$, $R^{10}$ and A are as defined above.

Preference is furthermore given to compounds of the formula (I-d)

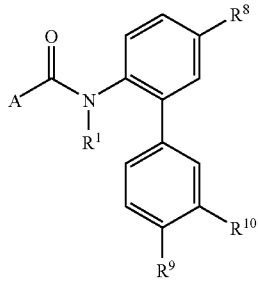

(I-d)

in which $R^1$, $R^8$, $R^9$, $R^{10}$ and A are as defined above.

Preference is furthermore given to compounds of the formula (I-e)

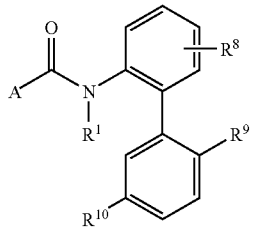

(I-e)

in which $R^1$, $R^8$, $R^9$, $R^{10}$ and A are as defined above.

Preference is furthermore given to compounds of the formula (I-f)

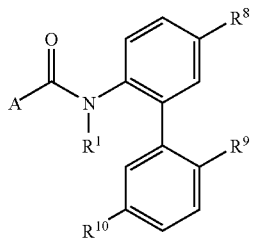

(I-f)

in which $R^1$, $R^8$, $R^9$, $R^{10}$ and A are as defined above.

Preference is furthermore given to compounds of the formulae (I) and (I-b) to (I-f), in which $R^1$ represents hydrogen.

Preference is furthermore given to compounds of the formulae (I) and (I-b) to (I-f), in which $R^8$ represents hydrogen.

Preference is furthermore given to compounds of the formulae (I) and (I-b) to (I-f), in which $R^8$ represents fluorine.

However, the general or preferred radical definitions or illustrations given above can also be combined with one another as desired, i.e. including combinations between the respective ranges and preferred ranges. They apply to the end products and, correspondingly, to the precursors and intermediates.

Using, for example, 1-methyl-3-(trifluoromethyl)-1H-pyrazole-4-carbonyl chloride and methyl 2'-amino-3,5'-difluorobiphenyl-4-carboxylate as starting materials and a base, the course of the process (a) according to the invention can be illustrated by the reaction equation below:

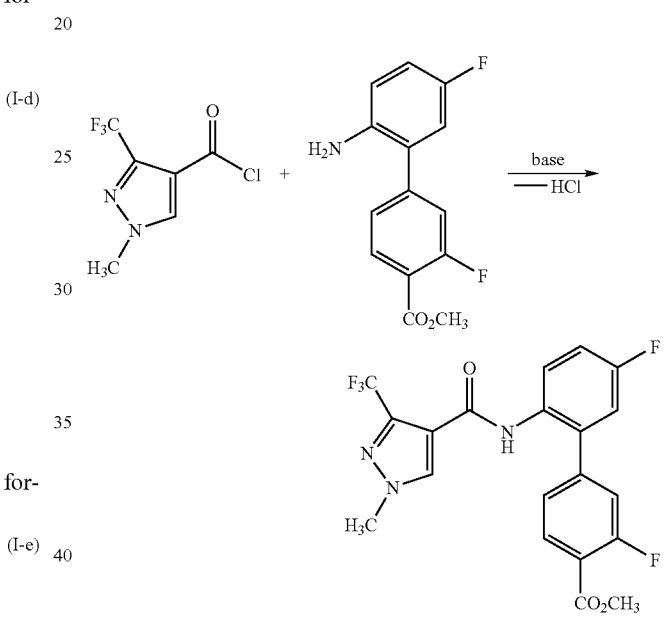

The formula (II) provides a general definition of the carbonyl halides required as starting materials for carrying out the process (a) according to the invention. In this formula (II), A preferably, particularly preferably, very particularly preferably and especially preferably has those meanings which have already been mentioned in connection with the description of the compounds of the formula (I) according to the invention as being preferred, particularly preferred, etc., for this radical. $X^1$ preferably represents fluorine, chlorine or hydroxyl, particularly preferably chlorine or hydroxyl.

The carbonyl halides of the formula (II) are known and/or can be prepared by known processes (cf., for example, EP-A 0 545 099, JP-A 01-290662 and U.S. Pat. No. 5,093,347).

The formula (III) provides a general definition of the amines furthermore required as starting materials for carrying out the process (a) according to the invention. In this formula (III), $R^1$, $R^8$, $R^9$ and $R^{10}$ preferably, particularly preferably, very particularly preferably and especially preferably have those meanings which have already been mentioned in connection with the description of the compounds of the formula (I) according to the invention as being preferred, particularly preferred, etc., for this radical.

The amines of the formulae (III-1), (III-2) and (III-3) are novel (III-1)
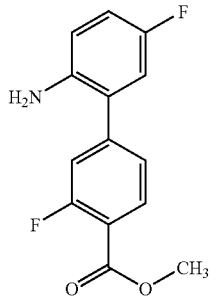

(III-2)
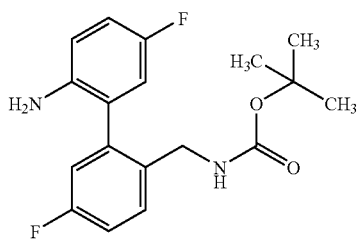

(III-3)
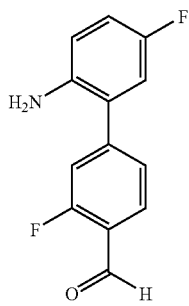

Amines of the formulae (III-1), (III-2) and (III-3) can be prepared by known processes (cf. WO 01/53259 and WO 01/49664, see also the Preparation Examples).

Using methyl 3,5'-difluoro-2'-({[1-methyl-3-(trifluoromethyl)-1H-pyrazol-4-yl]carbonyl}amino)-biphenyl-4-carboxylate and acetyl chloride as starting materials, the course of the process (b) according to the invention can be illustrated by the formula scheme below:

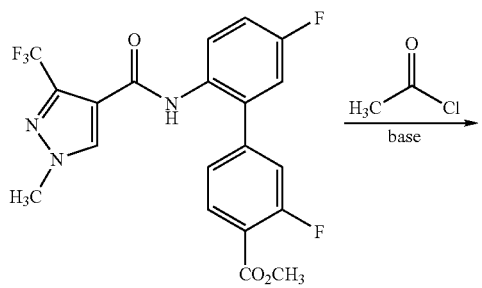

-continued

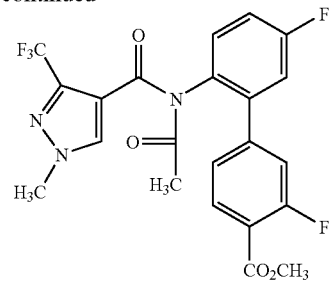

The formula (I-a) provides a general definition of the biphenylcarboxamides required as starting materials for carrying out the process (b) according to the invention. In this formula (I-a), $R^8$, $R^9$, $R^{10}$ and A preferably, particularly preferably, very particularly preferably and especially preferably have those meanings which have already been mentioned in connection with the description of the compounds of the formula (I) according to the invention as being preferred, particularly preferred, etc., for these radicals.

The compounds of the formula (I-a) are compounds according to the invention and can be prepared according to process (a).

The formula (IV) provides a general definition of the halides furthermore required as starting materials for carrying out the process (b) according to the invention. In this formula (IV), $R^{1-B}$ preferably, particularly preferably, very particularly preferably and especially preferably has those meanings which have already been mentioned above for the radical $R^1$ as being preferred, particularly preferred, etc., where $R^{1-B}$ never represents hydrogen. Hal represents chlorine, bromine or iodine.

Halides of the formula (IV) are known.

Suitable diluents for carrying out the process (a) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloro-methane, chloroform, carbon tetrachloride, dichloroethane or trichloroethane; ethers, such as diethyl ether, diisopropyl ether, methyl t-butyl ether, methyl-t-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; mixtures thereof with water or pure water.

The process (a) according to the invention is, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium amide, lithium diisopropylamide, sodium methoxide, sodium ethoxide, potassium tert-butoxide, sodium hydroxide, potassium hydroxide, sodium acetate, sodium carbonate, potassium carbonate, potassium bicarbonate, sodium bicarbonate or ammonium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N- dimethylaminopyridine, diazabicyclooctane (DABCO), diazabicyclononene (DBN) or diazabicycloundecene (DBU).

The process (a) according to the invention is, if appropriate, carried out in the presence of a suitable coupling agent (if $X^5$ represents hydroxyl). Suitable coupling agents are all customary carbonyl activators. These preferably include N-[3-(dimethylamino)propyl]-N'-ethylcarbodiimide hydrochloride, N,N'-di-sec-butylcarbodiimide, N,N'-dicyclohexylcarbodiimide, N,N'-diisopropylcarbodiimide, 1-(3-(dimethylamino)propyl)-3-ethylcarbodiimide methiodide, 2-bromo-3-ethyl-4-methylthiazolium tetrafluoroborate, N,N-bis[2-oxo-3-oxazolidinyl]phosphorodiamidic chloride, chlorotripyrrolidinophos-phonium hexafluorophosphate, bromotripyrrolidinophosphonium hexafluorophosphate, O-(1H-benzotriazol-1-yloxy)tris(dimethylamino)phosphonium hexafluorophosphate, O-(1H-benzotriazol-1-yl)-N,N,N',N'-tetramethyluronium hexafluorophosphate, O-(1H-benzotriazol-1-yl)-N,N,N',N'-bis(tetra-methylene)uronium hexafluorophosphate, O-(1H-benzotriazol-1-yl)-N,N,N',N'-bis(tetramethylene)-uronium tetrafluoroborate, N,N,N',N'-bis(tetramethylene)chlorouronium tetrafluoroborate, O-(7-aza-benzotriazol-1-yl)-N,N,N,N-tetramethyluronium hexafluorophosphate and 1-hydroxybenzotriazole. These reagents can be employed separately, but also in combination.

When carrying out the process (a) according to the invention, the reaction temperatures can be varied within a relatively wide range. In general, the process is carried out at temperatures of from 0° C. to 150° C., preferably at temperatures of from 20° C. to 110° C.

For carrying out the process (a) according to the invention for preparing the compounds of the formula (I), in general from 0.2 to 5 mol, preferably from 0.5 to 2 mol, of aniline derivative of the formula (III) are employed per mole of the carbonyl halide of the formula (II). Work-up is carried out by customary methods.

Suitable diluents for carrying out the process (b) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole, or amides, such as N,N-dimethylformamide, N,N-dimethylacetamide, N-methylformanilide, N-methylpyrrolidone or hexamethylphosphoric triamide.

The process (b) according to the invention is carried out in the presence of a base. Suitable bases are all customary inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, potassium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or caesium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclo-nonene (DBN) or diazabicycloundecene (DBU).

When carrying out the process (b) according to the invention, the reaction temperatures can be varied within a relatively wide range. In general, the process is carried out at temperatures of from 0° C. to 150° C., preferably at temperatures of from 20° C. to 110° C.

For carrying out the process (b) according to the invention for preparing the compounds of the formula (I), in general from 0.2 to 5 mol, preferably from 0.5 to 2 mol, of halide of the formula (IV) are employed per mole of the biphenylcarboxamide of the formula (I-a).

In general, the processes (a) and (b) according to the invention are carried out under atmospheric pressure. However, it is also possible to operate under elevated or reduced pressure—in general between 0.1 bar and 10 bar.

The compounds according to the invention exhibit a potent microbicidal activity and can be employed in crop protection and in the protection of materials for controlling undesirable microorganisms such as fungi and bacteria.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Examples which may be mentioned, but not by limitation, of some pathogens of fungal and bacterial diseases which come under the abovementioned general terms are:

diseases caused by powdery mildew pathogens, such as, for example, *Blumeria* species such as, for example, *Blumeria graminis*; *Podosphaera* species such as, for example, *Podosphaera leucotricha*; *Sphaerotheca* species such as, for example, *Sphaerotheca fuliginea*; *Uncinula* species such as, for example, *Uncinula necator*;

diseases caused by rust pathogens such as, for example, *Gymnosporangium* species such as, for example, *Gymnosporangium sabinae Hemileia* species such as, for example, *Hemileia vastatrix*; *Phakopsora* species such as, for example, *Phakopsora pachyrhizi* and *Phakopsora meibomiae*; *Puccinia* species such as, for example, *Puccinia recondita* or *Puccinia graminis*; *Uromyces* species such as, for example, *Uromyces appendiculatus*;

diseases caused by pathogens from the Oomycetes group such as, for example, *Bremia* species such as, for example, *Bremia lactucae*; *Peronospora* species such as, for example, *Peronospora pisi* or *P. brassicae*; *Phytophthora* species such as, for example, *Phytophthora infestans*; *Plasmopara* species such as, for example, *Plasmopara viticola*; *Pseudoperonospora* species such as, for example, *Pseudoperonospora humuli* or *Pseudoperonospora cubensis*; *Pythium* species such as, for example, *Pythium ultimum*;

leaf spot diseases and leaf wilts caused by, for example, *Alternaria* species such as, for example, *Alternaria solani*; *Cercospora* species such as, for example, *Cercospora beticola*; *Cladosporium* species such as, for example, *Cladosporium cucumerinum*; *Cochliobolus* species such as, for example, *Cochliobolus sativus* (conidial form: *Drechslera*, syn: *Helminthosporium*); *Colletotrichum* species such as, for example, *Colletotrichum lindemuthanium*; *Cycloconium* species such as, for example, *Cycloconium oleaginum*; *Diaporthe* species such as, for example, *Diaporthe citri*; *Elsinoe* species such as, for example, *Elsinoe fawcettii*; *Gloeosporium* species such as, for example, *Gloeosporium laeticolor*; *Glomerella* species such as, for example, *Glomerella cingulata*; *Guignardia* species such as, for example,

*Guignardia bidwelli; Leptosphaeria* species such as, for example, *Leptosphaeria maculans; Magnaporthe* species such as, for example, *Magnaporthe grisea; Mycosphaerella* species such as, for example, *Mycosphaerella graminicola* and *Mycosphaerella fijiensis; Phaeosphaeria* species such as, for example, *Phaeosphaeria nodorum; Pyrenophora* species such as, for example, *Pyrenophora teres; Ramularia* species such as, for example, *Ramularia collo-cygni; Rhynchosporium* species such as, for example, *Rhynchosporium secalis; Septoria* species such as, for example, *Septoria apii; Typhula* species such as, for example, *Typhula incarnata; Venturia* species such as, for example, *Venturia inaequalis;* root and stem diseases caused by, for example, *Corticium* species such as, for example, *Corticium graminearum; Fusarium* species such as, for example, *Fusarium oxysporum; Gaeumannomyces* species such as, for example, *Gaeumannomyces graminis; Rhizoctonia* species such as, for example, *Rhizoctonia solani; Tapesia* species such as, for example, *Tapesia acuformis* or *Tapesia yallundae; Thielaviopsis* species such as, for example, *Thielaviopsis basicola;* ear and panicle diseases (including maize cobs), caused by, for example, *Alternaria* species such as, for example, *Alternaria* spp.; *Aspergillus* species such as, for example, *Aspergillus flavus; Cladosporium* species such as, for example, *Cladosporium cladosporioides; Claviceps* species such as, for example, *Claviceps purpurea; Fusarium* species such as, for example, *Fusarium culmorum; Gibberella* species such as, for example, *Gibberella zeae; Monographella* species such as, for example, *Monographella nivalis;* diseases caused by smuts such as, for example, *Sphacelotheca* species such as, for example, *Sphacelotheca reiliana; Tilletia* species such as, for example, *Tilletia caries; Urocystis* species such as, for example, *Urocystis occulta; Ustilago* species such as, for example, *Ustilago nuda;* fruit rots caused by, for example, *Aspergillus* species such as, for example, *Aspergillus flavus; Botrytis* species such as, for example, *Botrytis cinerea; Penicillium* species such as, for example, *Penicillium expansum* and *Penicillium purpurogenum; Sclerotinia* species such as, for example, *Sclerotinia sclerotiorum; Verticilium* species such as, for example, *Verticilium alboatrum;* seed- and soil-borne rots and wilts, and seedling diseases, caused by, for example, *Fusarium* species such as, for example, *Fusarium culmorum; Phytophthora* species such as, for example, *Phytophthora cactorum; Pythium* species such as, for example, *Pythium ultimum; Rhizoctonia* species such as, for example, *Rhizoctonia solani; Sclerotium* species such as, for example, *Sclerotium rolfsii;* cankers, galls and witches' broom disease, caused by, for example, *Nectria* species such as, for example, *Nectria galligena;*

Wilts caused by, for example, *Monilinia* species such as, for example, *Monilinia laxa;* deformations of leaves, flowers and fruits, caused by, for example, *Taphrina* species such as, for example, *Taphrina deformans;* degenerative diseases of woody species, caused by, for example, Esca species such as, for example, *Phaeomoniella chlamydospora* and *Phaeoacremonium aleophilum* and *Fomitiporia mediterranea;* diseases of inflorescences and seeds, caused by, for example, *Botrytis* species such as, for example, *Botrytis cinerea;* diseases of the plant tubers, caused by, for example, *Rhizoctonia* species such as, for example, *Rhizoctonia solani; Helminthosporium* species, such as, for example, *Helminthosporium solani;* diseases caused by bacterial pathogens such as, for example, *Xanthomonas* species such as, for example, *Xanthomonas campestris* pv. *oryzae; Pseudomonas* species such as, for example, *Pseudomonas syringae* pv. *lachrymans; Erwinia* species such as, for example, *Erwinia amylovora.*

The following diseases of soybeans can preferably be controlled:

Fungal diseases on leaves, stems, pods and seeds caused by, for example, alternaria leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi*), scab (*Sphaceloma glycines*), stemphylium leaf blight (*Stemphylium botryosum*), target spot (*Corynespora cassiicola*);

fungal diseases on roots and the stem base caused by, for example, black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmo-spora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The active compounds according to the invention also have a potent strengthening effect in plants. They are therefore suitable for mobilizing the plants' defences against attack by undesired microorganisms.

Plant-strengthening (resistance-inducing) substances are understood as meaning, in the present context, those substances which are capable of stimulating the defence system of plants in such a way that, when subsequently inoculated with undesired microorganisms, the treated plants display a substantial degree of resistance to these microorganisms.

In the present case, undesired microorganisms are understood as meaning phytopathogenic fungi, bacteria and viruses. Thus, the compound according to the invention can be employed for protecting plants against attack by the above-mentioned pathogens within a certain period of time after the treatment. The period of time within which protection is effected generally extends from 1 to 28 days, preferably 1 to 14 days particularly preferably 1 to 7 days, after the plants have been treated with the active compounds.

The fact that the active compounds, at the concentrations required for the controlling of plant diseases, are well tolerated by plants permits the treatment of aerial plant parts, of vegetative propagation material and seed, and of the soil.

In this context, the active compounds according to the invention can be employed particularly successfully for controlling cereal diseases such as, for example, against *Puccinia* species and of diseases in viticulture, fruit production and vegetable production such as, for example, against *Botrytis, Venturia* or *Alternaria* species.

The active compounds according to the invention are also suitable for increasing the yield. Moreover, they display a low degree of toxicity and are well tolerated by plants.

If appropriate, the active compounds according to the invention can also be used in certain concentrations and application rates as herbicides, for influencing plant growth and for controlling animal pests. If appropriate, they can also be employed as intermediates and precursors for the synthesis of further active compounds.

All plants and plant parts can be treated in accordance with the invention. Plants are understood as meaning, in the present context, all plants and plant populations, such as desired and undesired wild plants or crop plants (including naturally occurring crop plants). Crop plants may be plants which can be obtained by conventional breeding and optimization methods or else by biotechnological and genetic engineering methods or by combinations of these methods, including the transgenic plants and including the plant varieties capable or not capable of being protected by Plant Breeders' rights. Plant parts are understood as meaning all aerial and subterranean parts and organs of the plants, such as shoot, leaf, flower and root, examples which may be mentioned being leaves, needles, stalks, stems, flowers, fruiting bodies, fruits and seeds, and also roots, tubers and rhizomes. The plant parts also include harvested material and vegetative and generative propagation material, for example cuttings, tubers, rhizomes, slips and seeds.

The treatment according to the invention with the active compounds, of the plants and plant parts, is carried out directly or by acting on their environment, habitat, or store by the customary treatment methods, for example by immersion, spraying, vaporizing, fogging, broadcasting, painting on and, in the case of propagation material, in particular in the case of seeds, furthermore by coating with one or more coats.

In the protection of materials, the compounds according to the invention can be employed for protecting industrial materials against attack and destruction by undesired microorganisms. In the present context, industrial materials are understood as meaning non-live materials which have been made for use in technology. For example, industrial materials which are to be protected by active compounds according to the invention from microbial modification or destruction can be glues, sizes, paper and board, textiles, leather, timber, paints and plastic articles, cooling lubricants and other materials which are capable of being attacked or destroyed by microorganisms. Parts of production plants, for example cooling-water circuits, which can be adversely affected by the multiplication of microorganisms may also be mentioned within the materials to be protected. Industrial materials which may be mentioned with preference for the purposes of the present invention are glues, sizes, paper and board, leather, timber, paints, cooling lubricants and heat-transfer fluids, especially preferably wood.

Microorganisms which are capable of bringing about a degradation or modification of the industrial materials and which may be mentioned are, for example, bacteria, fungi, yeasts, algae and slime organisms. The active compounds according to the invention are preferably active against fungi, in particular moulds, wood-discolouring and wood-destroying fungi (Basidiomycetes) and against slime organisms and algae.

Examples which may be mentioned are microorganisms of the following genera:

*Alternaria* such as *Alternaria tenuis, Aspergillus* such as *Aspergillus niger, Chaetomium* such as *Chaetomium globosum, Coniophora* such as *Coniophora puetana, Lentinus* such as *Lentinus tigrinus, Penicillium* such as *Penicillium glaucum, Polyporus* such as *Polyporus versicolor, Aureobasidium* such as *Aureobasidium pullulans, Sclerophoma* such as *Sclerophoma pityophila, Trichoderma* such as *Trichoderma viride, Escherichia* such as *Escherichia coli, Pseudomonas* such as *Pseudomonas aeruginosa, Staphylococcus* such as *Staphylococcus aureus.*

Depending on their respective physical and/or chemical properties, the active compounds can be converted to the customary formulations, such as solutions, emulsions, suspensions, powders, foams, pastes, granules, aerosols, very fine capsules in polymeric substances and in coating compositions for seed, and also ULV cold- and warm-fogging formulations.

These formulations are produced in a known manner, for example by mixing the active compounds with extenders, that is liquid solvents, pressurized liquefied gases and/or solid carriers, optionally with the use of surface-active agents, that is emulsifiers and/or dispersants, and/or foam formers. If the extender used is water, it is also possible to employ for example organic solvents as cosolvents. Suitable liquid solvents are essentially: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, and also water. Liquefied gaseous extenders or carriers are those liquids which are gaseous at ambient temperature and at atmospheric pressure, for example aerosol propellants such as halogenated hydrocarbons and also butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as finely divided silica, alumina and silicates. As solid carriers for granules there are suitable: for example crushed and fractionated natural rocks such as calcite, pumice, marble, sepiolite and dolomite, and also synthetic granules of inorganic and organic meals, and granules of organic material such as sawdust, coconut shells, maize cobs and tobacco stalks. As emulsifiers and/or foam formers there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates. As dispersants there are suitable: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in their formulations, can also be used as a mixture with known fungicides, bactericides, acaricides, nematicides, or insecticides, for example, to broaden the activity spectrum or prevent the development of resistance. In many instances, synergistic effects are obtained, i.e. the activity of the mixture exceeds the activity of the individual components.

Examples of Co-Components in Mixtures are the Following Compounds

Fungicides:

1) Nucleic acid synthesis inhibitors: for example benalaxyl, benalaxyl-M, bupirimate, clozylacon, dimethirimol, ethirimol, furalaxyl, hymexazol, mefenoxam, metalaxyl, metalaxyl-M, ofurace, oxadixyl, oxolinic acid;

2) mitosis and cell division inhibitors: for example benomyl, carbendazim, diethofencarb, ethaboxam, fuberidazole, pencycuron, thiabendazole, thiophanate-methyl, zoxamide;

3) respiration inhibitors (inhibitors of the respiratory chain):

3.1) inhibitors which act on complex I of the respiratory chain: for example diflumetorim;

3.2) inhibitors which act on complex II of the respiratory chain: for example boscalid/nicobifen, carboxin, fenfuram, flutolanil, furametpyr, furmecyclox, mepronil, oxycarboxin, penthiopyrad, thifluzamide;

3.3) inhibitors which act on complex III of the respiratory chain: for example amisulbrom, azoxystrobin, cyazofamid, dimoxystrobin, enestrobin, famoxadone, fenamidone, fluoxastrobin, kresoxim-methyl, metominostrobin, orysastrobin, picoxystrobin, pyraclostrobin, trifloxystrobin;

4) decouplers: for example dinocap, fluazinam, meptyldinocap;

5) ATP production inhibitors: for example fentin acetate, fentin chloride, fentin hydroxide, silthiofam;

6) amino acid and protein biosynthesis inhibitors: for example andoprim, blasticidin-S, cyprodinil, kasugamycin, kasugamycin hydrochloride hydrate, mepanipyrim, pyrimethanil;

7) signal transduction inhibitors: for example fenpiclonil, fludioxonil, quinoxyfen;

8) lipid and membrane synthesis inhibitors: for example biphenyl, chlozolinate, edifenphos, iodocarb, iprobenfos, iprodione, isoprothiolane, procymidone, propamocarb, propamocarb hydrochloride, pyrazophos, tolclofos-methyl, vinclozolin;

9) ergosterol biosynthesis inhibitors: for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, prochloraz, propiconazole, prothioconazole, pyributicarb, pyrifenox, simeconazole, spiroxamine, tebuconazole, terbinafine, tetraconazole, triadimefon, triadimenol, tridemorph, triflumizole, triforine, triticonazole, uniconazole, viniconazole, voriconazole;

10) cell wall synthesis inhibitors: for example benthiavalicarb, dimethomorph, flumorph, iprovalicarb, polyoxins, polyoxorim, validamycin A;

11) melanin biosynthesis inhibitors: for example carpropamid, diclocymet, fenoxanil, phthalide, pyroquilon, tricyclazole;

12) resistance inductors: for example acibenzolar-S-methyl, probenazole, tiadinil;

13) compounds with multi-site activity: for example Bordeaux mixture, captafol, captan, chlorothalonil, copper naphthenate, copper oxide, copper oxychloride, copper preparations such as, for example, copper hydroxide, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propineb, sulphur and sulphur preparations such as, for example, calcium polysulphide, thiram, tolylfluanid, zineb, ziram;

14) a compound selected from the following enumeration: N-methyl-(2E)-2-(2-{[6-(3-chloro-2-methylphenoxy)-5-fluoropyrimidin-4-yl]oxy}phenyl)-2-(methoxyimino)acetamide, N-methyl-(2E)-2-{2-[({[(1E)-1-(3-{[(E)-1-fluoro-2-phenylvinyl]oxy}phenyl)ethylidene]amino}oxy)methyl]phenyl}-2-(methoxyimino)acetamide, 1-(4-chlorophenyl)-2-(1H-1,2,4-triazol-1-yl)cycloheptanol, 1-[(4-methoxyphenoxy)methyl]-2,2-dimethylpropyl-1H-imidazole-1-carboxylate, 2-(4-chlorophenyl)-N-{2-[3-methoxy-4-(prop-2-yn-1-yloxy)phenyl]ethyl}-2-(prop-2-yn-1-yloxy)acetamide, 2,3,5,6-tetrachloro-4-(methylsulphonyl)pyridine, 2-butoxy-6-iodo-3-propyl-4H-chromen-4-one, 2-chloro-N-(1,1,3-trimethyl-2,3-dihydro-1H-inden-4-yl)nicotinamide, 2-phenylphenol and salts thereof, 3,4,5-trichloro-pyridine-2,6-dicarbonitrile, 3,4-dichloro-N-(2-cyanophenyl)isothiazole-5-carboxamide, 3-[5-(4-chlorophenyl)-2,3-dimethylisoxazolidin-3-yl]pyridine, 5-chloro-6-(2,4,6-trifluorophenyl)-N-[(1R)-1,2,2-trimethylpropyl][1,2,4]triazolo[1,5-a]pyrimidine-7-amine, 5-chloro-7-(4-methylpiperidin-1-yl)-6-(2,4,6-trifluorophenyl)[1,2,4]triazolo[1,5-a]pyrimidine, 5-chloro-N-[(1R)-1,2-dimethylpropyl]-6-(2,4,6-trifluorophenyl)[1,2,4]triazolo[1,5-a]pyrimidine-7-amine, 8-hydroxyquinoline sulphate, benthiazole, bethoxazin, capsimycin, carvone, quinomethionate, cufraneb, cyflufenamid, cymoxanil, dazomet, debacarb, dichlorophen, diclomezine, dicloran, difenzoquat, difenzoquat methylsulphate, diphenylamine, ferimzone, flumetover, fluopicolide, fluoroimide, flusulfamide, fosetyl-aluminium, fosetyl-calcium, fosetyl-sodium, hexachlorobenzene, irumamycin, methasulfocarb, methyl (2-chloro-5-{(1E)-N-[(6-methylpyridin-2-yl)methoxy]ethanimidoyl}benzyl)carbamate, methyl (2E)-2-{2-[({cyclopropyl[(4-methoxyphenyl)imino]methyl}thio)methyl]phenyl}-3-methoxyacrylate, methyl 1-(2,2-dimethyl-2,3-dihydro-1H-inden-1-yl)-1H-imidazole-5-carboxylate, methyl 3-(4-chlorophenyl)-3-{[N-(isopropoxycarbonyl)valyl]amino}propanoate, methyl isothiocyanate, metrafenone, mildiomycin, N-(3',4'-dichloro-5-fluorobiphenyl-2-yl)-3-(difluoromethyl)-1-methyl-1H-pyrazole-4-carboxamide, N-(3-ethyl-3,5,5-trimethylcyclohexyl)-3-(formylamino)-2-hydroxybenzamide, N-(4-chloro-2-nitrophenyl)-N-ethyl-4-methylbenzenesulphonamide, N-[(5-bromo-3-chloropyridin-2-yl)methyl]-2,4-dichloronicotinamide, N-[1-(5-bromo-3-chloropyridin-2-yl)ethyl]-2,4-dichloronicotin-amide, N-[1-(5-bromo-3-chloropyridin-2-yl)ethyl]-2-fluoro-4-iodonicotinamide, N-[2-(4-{[3-(4-chlorophenyl)prop-2-yn-1-yl]oxy}-3-methoxyphenyl)ethyl]-N$^2$-(methylsulphonyl) valinamide, N-{(Z)-[(cyclopropylmethoxy)imino][6-(difluoromethoxy)-2,3-difluorophenyl]methyl}-2-phenylacetamide, N-{2-[3-chloro-5-(trifluoromethyl)pyridin-2-yl]ethyl}-2-(trifluoromethyl)benzamide, natamycin, nickel dimethyl dithiocarbamate, nitrothal-isopropyl, O-{1-[(4-methoxyphenoxy)methyl]-2,2-dimethylpropyl}1H-imidazole-1-carbothioate, octhilinone, oxamocarb, oxyfenthiin, pentachlorophenol and salts, phosphoric acid and its salts, piperalin, propamocarb fosetylate, propanosine-sodium, proquinazid, pyrrolnitrine, quintozene, tecloftalam, tecnazene, triazoxide, trichlamide, zarilamid.

Bactericides:

Bronopol, dichlorophen, nitrapyrin, nickel dimethyl dithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

1. Acetylcholine Esterase (Ache) Inhibitors 1.1 Carbamates (for example alanycarb, aldicarb, aldoxycarb, allyxycarb, aminocarb, azamethiphos, bendiocarb, benfuracarb, bufencarb, butacarb, butocarboxim, butoxycarboxim, carbaryl, carbofuran, carbosulfan, chloethocarb, coumaphos, cyanofenphos, cyanophos, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, triazamate, trimethacarb, XMC, xylylcarb)

1.2 Organophosphates (for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion)

2. Sodium Channel Modulators/Voltage-Dependent Sodium Channel Blockers 2.1 Pyrethroids (for example acrinathrin, allethrin (d-cis-trans, d-trans), beta-cyfluthrin, bifenthrin, bioallethrin, bioallethrin-S-cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, DDT, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R transisomer), prallethrin, profluthrin, protrifenbute, pyresmethrin, resmethrin, RU 15525, silafluofen, tau-fluvalinate, tefluthrin, terallethrin, tetramethrin (1R isomer), tralomethrin, transfluthrin, ZXI 8901, pyrethrins (pyrethrum))

2.2 Oxadiazines (for example indoxacarb)

3. Acetylcholine Receptor Agonists/Antagonists 3.1 Chloronicotinyls/neonicotinoids (for example acetamiprid, clothianidin, dinotefuran, imidacloprid, nitenpyram, nithiazine, thiacloprid, thiamethoxam)

3.2 Nicotine, bensultap, cartap

4. Acetylcholine Receptor Modulators 4.1 Spinosyns (for example spinosad)

5. GABA-Controlled Chloride Channel Antagonists 5.1 Cyclodiene organochlorines (for example camphechlor, chlordane, endosulfan, gamma-HCH, HCH, heptachlor, lindane, methoxychlor 5.2 Fiproles (for example acetoprole, ethiprole, fipronil, vaniliprole)

6. Chloride Channel Activators 6.1 Mectins (for example abamectin, avermectin, emamectin, emamectin benzoate, ivermectin, milbemectin, milbemycin)

7. Juvenile Hormone Mimetics (for example diofenolan, epofenonane, fenoxycarb, hydroprene, kinoprene, methoprene, pyriproxifen, triprene)

8. Ecdysone Agonists/Disruptors 8.1 Diacylhydrazines (for example chromafenozide, halofenozide, methoxyfenozide, tebufenozide)

9. Chitin Biosynthesis Inhibitors 9.1 Benzoylureas (for example bistrifluoron, chlofluazuron, diflubenzuron, fluazuron, flucycloxuron, flufenoxuron, hexaflumuron, lufenuron, novaluron, noviflumuron, penfluoron, teflubenzuron, tri-flumuron)

9.2 Buprofezin 9.3 Cyromazine

10. Inhibitors of Oxidative Phosphorylation, ATP Disruptors 10.1 Diafenthiuron 10.2 Organotins (for example azocyclotin, cyhexatin, fenbutatin oxide)

11. Uncouplers of Oxidative Phosphorylation by Interrupting the H-Proton Gradient 11.1 Pyrroles (for example chlorfenapyr)

11.2 Dinitrophenols (for example binapacyrl, dinobuton, dinocap, DNOC)

12. Site-I Electron Transport Inhibitors 12.1 METIs (for example fenazaquin, fenpyroximate, pyrimidifen, pyridaben, tebufenpyrad, tolfenpyrad)

12.2 Hydramethylnone 12.3 Dicofol

13. Site-II Electron Transport Inhibitors 13.1 Rotenone

14. Site-III Electron Transport Inhibitors 14.1 Acequinocyl, fluacrypyrim

15. Microbial Disruptors of the Insect Gut Membrane

*Bacillus thuringiensis* strains

16. Fat Synthesis Inhibitors 16.1 Tetronic acids (for example spirodiclofen, spiromesifen)

16.2 Tetramic acids [for example 3-(2,5-dimethylphenyl)-8-methoxy-2-oxo-1-azaspiro[4.5]dec-3-en-4-yl ethyl carbonate (also known as: carbonic acid, 3-(2,5-dimethylphenyl)-8-methoxy-2-oxo-1-azaspiro[4.5]dec-3-en-4-yl ethyl ester, CAS Reg. No.: 382608-10-8) and carbonic acid, cis-3-(2,5-dimethylphenyl)-8-methoxy-2-oxo-1-azaspiro[4.5]dec-3-en-4-yl ethyl ester (CAS Reg.-No.: 203313-25-1)]

17. Carboxamides (for example flonicamid)

18. Octopaminergic Agonists (for example amitraz)

19. Inhibitors of Magnesium-Stimulated ATPase (for example propargite)

20. Ryanodine Receptor Agonists 20.1 Benzoic dicarboxamides [for example $N^2$-[1,1-dimethyl-2-(methylsulphonyl)ethyl]-3-iodo-N'-[2-methyl-4-[1,2,2,2-tetrafluoro-1-(trifluoromethyl)ethyl]phenyl]-1,2-benzenedicarboxamide (CAS Reg. No.: 272451-65-7), flubendiamide)

20.2 Anthranilamides (for example DPx E2Y45=3-bromo-N-{4-chloro-2-methyl-6-[(methylamino)carbonyl]phenyl}-1-(3-chloropyridin-2-yl)-1H-pyrazole-5-carboxamide)

21. Nereistoxin Analogues (for example thiocyclam hydrogen oxalate, thiosultap sodium)

22. Biologicals, Hormones or Pheromones (for example azadirachtin, *Bacillus* spec., *Beauveria* spec., codlemone, *Metarrhizium* spec., *Paecilomyces* spec., thuringiensin, *Verticillium* spec.)

23. Active Compounds with Unknown or Unspecific Mechanisms of Action 23.1 Fumigants (for example aluminium phosphide, methyl bromide, sulphuryl fluoride)

23.2 Selective antifeedants (for example cryolite, flonicamid, pymetrozine)

23.3 Mite growth inhibitors (for example clofentezine, etoxazole, hexythiazox)

23.4 Amidoflumet, benclothiaz, benzoximate, bifenazate, bromopropylate, buprofezin, quino-methionate, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyrafluprole, pyridalyl, pyriprole, sulfluramid, tetradifon, tetrasul, triarathene, verbutin, furthermore the compound 3-methyl-phenyl propylcarbamate (tsumacide Z), the compound 3-(5-chloro-3-pyridinyl)-8-(2,2,2-trifluoroethyl)-8-azabicyclo[3.2.1]octane-3-carbonitrile (CAS Reg. No. 185982-80-3) and the corresponding 3-endo isomer (CAS Reg. No. 185984-60-5) (cf. WO 96/37494, WO 98/25923), and preparations which contain insecticidally active plant extracts, nematodes, fungi or viruses.

A mixture with other known active compounds such as herbicides, or with fertilizers and growth regulators, safeners or semiochemicals is also possible.

In addition, the compounds of the formula (I) according to the invention also have very good antimycotic activity. They have a very broad antimycotic spectrum of action, in particular against dermatophytes and budding fungi, moulds and diphasic fungi (for example against *Candida* species such as *Candida albicans, Candida glabrata*) and *Epidermophyton floccosum, Aspergillus* species such as *Aspergillus niger* and *Aspergillus fumigatus, Trichophyton* species such as *Trichophyton mentagrophytes, Microsporon* species such as *Microsporon canis* and audouinii. The enumeration of these fungi is no restriction whatsoever of the mycotic spectrum which can be controlled and is provided for illustration only.

The active compounds can be employed as such, in the form of their formulations or the use forms prepared therefrom, such as ready-to-use solutions, suspensions, wettable powders, pastes, soluble powders, dusts and granules. They are applied in the customary manner, for example by pouring, spraying, atomizing, broadcasting, dusting, foaming, painting on and the like. It is furthermore possible to apply the active compounds by the ultra-low-volume method, or to inject the active compound preparation or the active compound itself into the soil. The seed of the plants can also be treated.

When employing the active compounds according to the invention as fungicides, the application rates can be varied within a substantial range, depending on the type of application. In the treatment of plant parts, the application rates of active compound are generally between 0.1 and 10 000 g/ha, preferably between 10 and 1000 g/ha. For the treatment of seed, the application rates of active compound are generally between 0.001 and 50 g per kilogram of seed, preferably between 0.01 and 10 g per kilogram of seed. For treating the soil, the application rates of active compound are generally between 0.1 and 10 000 g/ha, preferably between 1 and 5000 g/ha.

As already mentioned above, all plants and their parts can be treated in accordance with the invention. In a preferred embodiment, plant species and plant varieties which are found in the wild or are obtained by traditional biological breeding methods, such as hybridization or protoplast fusion, and parts of the former are treated. In a further preferred embodiment, transgenic plants and plant varieties which have been obtained by recombinant methods, if appropriate in combination with traditional methods (genetically modified organisms) and their parts are treated. The term "parts" or "parts of plants" or "plant parts" has been illustrated above.

Particularly preferably, plants of the plant cultivars which are in each case commercially available or in use are treated according to the invention. Plant cultivars are understood as meaning plants with new properties ("traits") which have been obtained by conventional cultivation, by mutagenesis or else by recombinant DNA techniques. These may be cultivars, breeds, biotypes or genotypes.

Depending on the plant species or plant cultivars, their location and growth conditions (soils, climate, vegetation period, nutrition), the treatment according to the invention may also result in superadditive ("synergistic") effects. Thus, for example, reduced application rates and/or extensions of the activity spectrum and/or an increase in the activity of the substances and compositions that can be used according to the invention, better plant growth, more developed root system, higher resistance of the plant variety or plant cultivar, increased growth of shoots, higher plant vitality, increased tolerance to high or low temperatures, increased tolerance to drought or to water or soil salinity, increased flowering performance, easier harvesting, accelerated maturation, higher harvest yields, larger fruit, increased plant size, greener leaf colour, earlier blossoming, better quality and/or a higher nutritional value of the harvested products, higher sugar concentration in the fruits, better storage stability and/or processability of the harvested products which exceed the effects which were actually to be expected are possible.

The preferred transgenic plants or plant cultivars (i.e. those obtained by genetic engineering) which are to be treated according to the invention include all plants which, as a result of the recombinant modification, received genetic material which imparts particular advantageous useful properties ("traits") to these plants. Examples of such properties are better plant growth, increased tolerance to high or low temperatures, increased tolerance to drought or to water or soil salinity, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized in particular are increased defence of the plants against insects, arachnids, nematodes, slugs and snails as the result of toxins formed in the plants, in particular those formed in the plants by the genetic material from *Bacillus thuringiensis* (for example by the genes CryIA(a), CryIA (b), CryIA(c), CryIIA, CryIIIA, CryIIIB2, Cry9c, Cry2Ab, Cry3Bb and CryIF and also combinations thereof) (hereinbelow referred to as "Bt plants"). Traits which are also particularly emphasized are the increased defence of plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard®V (cotton), Nucoton® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned also include the varieties sold under the name Clearfield® (for example maize). Of course, these statements also apply to plant cultivars having these genetic traits or genetic traits still to be developed, which cultivars will be developed and/or marketed in the future.

The plants listed can be treated according to the invention in a particularly advantageous manner with the compounds of the general formula (I) or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The preparation and the use of the active compounds according to the invention is illustrated by the examples below.

PREPARATION EXAMPLES

Example 1

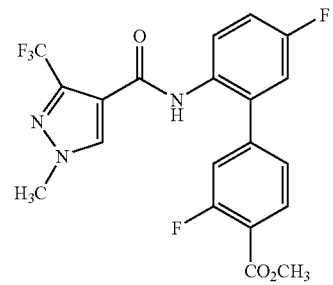

0.08 ml (0.88 mmol) of oxalyl dichloride is added to a suspension consisting of 155.3 mg (0.8 mmol) of 1-methyl-3-(trifluoromethyl)-1H-pyrazole-4-carboxylic acid in 5 ml of dichloromethane and 30 µl of dimethylformamide. The reaction mixture is stirred at room temperature for 2 hours, and a solution consisting of 210.6 mg (0.8 mmol) of methyl 2'-amino-3,5'-difluorobiphenyl-4-carboxylate and 0.16 ml (1.1 mmol) of triethylamine in 5 ml of dichloromethane is then added dropwise. The reaction mixture is stirred at room temperature for 16 hours and put into 4 ml of water, and the organic phase is dried over sodium sulphate and concentrated under reduced pressure. This gives 308 mg (0.7 mmol, 87% of theory) of methyl 3,5'-difluoro-2'-({[1-methyl-3-(trifluoromethyl)-1H-pyrazol-4-yl]carbonyl}amino)biphenyl-4-carboxylate (log P (pH 2.3) 2.64).

The compounds of the formula (I) listed in Table 1 below can be obtained analogously to Example 1 and in accordance with the general descriptions of the processes according to the invention.

TABLE 1

Structure (I): A-C(=O)-N(R¹)-[biphenyl with R⁸ on upper ring position 4, R⁹ and R¹⁰ on lower ring positions 3',4']

| No. | R¹ | R⁸ | R⁹ | R¹⁰ | A | logP (pH 2.3) |
|---|---|---|---|---|---|---|
| 1 | H | 4-F | 4'-CO₂CH₃ | 3'-F | 3-(CF₃)-4-methyl-1-methyl-1H-pyrazol-5-yl | 2.64 |
| 2 | H | 4-F | 4'-CO₂CH₃ | 3'-F | 3-(CHF₂)-4-methyl-1-methyl-1H-pyrazol-5-yl | 2.82 |
| 3 | H | 4-F | 2'-CH₂NHCO₂t-Bu | 5'-F | 3-(CF₃)-4-methyl-1-methyl-1H-pyrazol-5-yl | 3.59 |
| 4 | H | 4-F | 2'-CH₂NHCO₂t-Bu | 5'-F | 3-(CHF₂)-4-methyl-1-methyl-1H-pyrazol-5-yl | 3.38 |
| 5 | H | 4-F | 4'-CH₂NHCO₂t-Bu | 3'-F | 3-(CF₃)-4-methyl-1-methyl-1H-pyrazol-5-yl | |
| 6 | H | 4-F | 4'-CH₂NHCO₂t-Bu | 3'-F | 3-(CHF₂)-4-methyl-1-methyl-1H-pyrazol-5-yl | 3.39 |
| 7 | H | 4-F | 4'-C(O)H | 3'-F | 3-(CF₃)-4-methyl-1-methyl-1H-pyrazol-5-yl | |
| 8 | H | 4-F | 4'-C(O)H | 3'-F | 3-(CHF₂)-4-methyl-1-methyl-1H-pyrazol-5-yl | |
| 9 | H | H | 4'-SO₂N(CH₃)₂ | H | 3-(CHF₂)-4-methyl-1-methyl-1H-pyrazol-5-yl | 2.42 |
| 10 | H | 4-F | 4'-NHCO₂t-Bu | H | 3-(CHF₂)-4-methyl-1-methyl-1H-pyrazol-5-yl | |

Preparation of Starting Materials of the Formula (III)

Example (III-1)

Preparation of Starting Materials of the Formula (III)

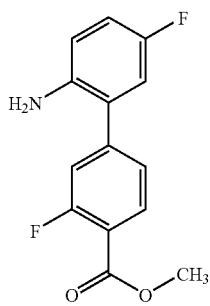

(III-1)

Under an atmosphere of inert gas (argon), 4.5 ml of a saturated sodium carbonate solution and 0.1 g (0.1 mmol) of tetrakis(triphenylphosphine)palladium(0) are added to a suspension consisting of 0.9 g (4.8 mmol) of 2-bromo-4-fluoroaniline and 1.0 g (5.1 mmol) of [3-fluoro-4-(methoxycarbonyl)phenyl]-boronic acid in 5 ml of toluene and 0.5 ml of ethanol. The reaction mixture is stirred at 80° C. for 16 hours and then poured into 10 ml of water and extracted with 20 ml of toluene. The combined organic phases are dried over magnesium sulphate, filtered and concentrated under reduced pressure. Column chromatography (gradient cyclohexane/ ethyl acetate) gives 0.5 g (1.76 mmol, 37% of theory) of methyl 2'-amino-3,5'-difluorobiphenyl-4-carboxylate [log P (pH 2.3) 2.73].

The compounds of the formula (III) listed in Table 2 below can be obtained analogously to Example (III-1) and in accordance with the general descriptions of the processes according to the invention.

TABLE 2

(III)

| No. | $R^8$ | $R^9$ | $R^{10}$ | logP (pH 2.3) |
|---|---|---|---|---|
| 9 | 4-F | 4'-CO$_2$CH$_3$ | 3'-F | 2.73 |
| 10 | 4-F | 2'-CH$_2$NHCO$_2$t-Bu | 5'-F | 3.29 |
| 11 | 4-F | 4'-C(O)H | 3'-F | 2.47 |
| 12 | H | 4'-CO$_2$CH$_3$ | CH$_3$ | 2.61 |

The logP values given in the Tables and Preparation Examples above are determined in accordance with EEC Directive 79/831 Annex V.A8 by HPLC (High Performance Liquid Chromatography) on a reverse-phase column (C 18). Temperature: 43° C.

The determination is carried out in the acidic range at pH 2.3 using the mobile phases 0.1% aqueous phosphoric acid and acetonitrile; linear gradient from 10% acetonitrile to 90% acetonitrile.

Calibration is carried out using unbranched alkan-2-ones (having 3 to 16 carbon atoms) with known logP values (determination of the logP values by the retention times using linear interpolation between two successive alkanones).

The lambda max values were determined in the maxima of the chromatographic signals using the UV spectra from 200 nm to 400 nm.

Use Examples

Example A

| | Venturia test (apple)/protective |
|---|---|
| Solvents: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvents and emulsifier, and the concentrate is diluted with water to the desired concentration.

To test for protective activity, young plants are sprayed with the active compound preparation at the stated application rate. After the spray coating has dried on, the plants are inoculated with an aqueous conidia suspension of the apple scab pathogen *Venturia inaequalis* and then remain in an incubation cabin at about 20° C. and 100% relative atmospheric humidity for 1 day. The plants are then placed in a greenhouse at about 21° C. and a relative atmospheric humidity of about 90%.

Evaluation is carried out 10 days after the inoculation. 0% means an efficacy which corresponds to that of the control, whereas an efficacy of 100% means that no infection is observed.

TABLE A

Venturia test (apple)/protective

| Active compound according to the invention | Application rate of active compound in ppm | Efficacy in % |
|---|---|---|
| (2) [structure shown] | 100 | 71 |

Example B

| Botrytis test (bean)/protective | |
|---|---|
| Solvents: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvents and emulsifier, and the concentrate is diluted with water to the desired concentration.

To test for protective activity, young plants are sprayed with the active compound preparation at the stated application rate. After the spray coating has dried on, 2 small pieces of agar colonized by Botrytis cinerea are placed onto each leaf. The inoculated plants are placed in a dark chamber at about 20° C. and 100% relative atmospheric humidity.

The size of the infected areas on the leaves is evaluated 2 days after the inoculation. 0% means an efficacy which corresponds to that of the control, whereas an efficacy of 100% means that no infection is observed.

TABLE B

Botrytis test (bean)/protective

| Active compound according to the invention | Application rate of active compound in ppm | Efficacy in % |
|---|---|---|
| (1) [structure: F₃C-pyrazole-C(O)NH-biphenyl with F, F, CO₂CH₃ substituents; N-CH₃] | 100 | 78 |

Example C

| Uromyces test (bean)/protective | |
|---|---|
| Solvents: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvents and emulsifier, and the concentrate is diluted with water to the desired concentration.

To test for protective activity, young plants are sprayed with the active compound preparation at the stated application rate. After the spray coating has dried on, the plants are inoculated with an aqueous spore suspension of the bean rust pathogen Uromyces appendiculatus and then remain in an incubation cabin at about 20° C. and 100% relative atmospheric humidity for 1 day. The plants are then placed in a greenhouse at about 21° C. and a relative atmospheric humidity of about 90%.

Evaluation is carried out 10 days after the inoculation. 0% means an efficacy which corresponds to that of the control, whereas an efficacy of 100% means that no infection is observed.

TABLE C

Uromyces test (bean)/protective

| Active compound according to the invention | Application rate of active compound in ppm | Efficacy in % |
|---|---|---|
| (1) [structure: F₃C-pyrazole-C(O)NH-biphenyl with F, F, CO₂CH₃ substituents; N-CH₃] | 100 | 93 |
| (2) [structure: F₂HC-pyrazole-C(O)NH-biphenyl with F, F, CO₂CH₃ substituents; N-CH₃] | 100 | 78 |

Example D

| Puccinia test (wheat)/protective | |
|---|---|
| Solvent: | 50 parts by weight of N,N-dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the active compound preparation at the stated application rate. After the spray coating has dried on, the plants are sprayed with a conidia suspension of Puccinia recondita. The plants remain in an incubation cabin at 20° C. and 100% relative atmospheric humidity for 48 hours.

The plants are then placed in a greenhouse at a temperature of about 20° C. and a relative atmospheric humidity of 80% to promote the development of rust pustules.

Evaluation is carried out 10 days after the inoculation. 0% means an efficacy which corresponds to that of the control, whereas an efficacy of 100% means that no infection is observed.

TABLE D

*Puccinia* test (wheat)/protective

| Active compound according to the invention | Application rate of active compound in ppm | Efficacy in % |
|---|---|---|
| 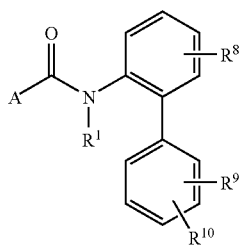 (1) | 1000 | 100 |
| (2) | 1000 | 90 |

The invention claimed is:

1. A biphenylcarboxamide of formula (I)

(1)

in which
$R^1$ represents hydrogen, $C_1$-$C_8$-alkyl, $C_1$-$C_6$-alkylsulphinyl, $C_1$-$C_6$-alkylsulphonyl, $C_1$-$C_4$-alkoxy-$C_1$-$C_4$-alkyl, $C_3$-$C_8$-cycloalkyl; $C_1$-$C_6$-haloalkyl, $C_1$-$C_4$-haloalkylthio, $C_1$-$C_4$-haloalkylsulphinyl, $C_1$-$C_4$-haloalkylsulphonyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$-alkyl)carbonyl-$C_1$-$C_3$-alkyl, halo-($C_1$-$C_3$-alkoxy)carbonyl-$C_1$-$C_3$-alkyl having in each case 1 to 13 fluorine, chlorine and/or bromine atoms;

($C_1$-$C_8$-alkyl)carbonyl, ($C_1$-$C_8$-alkoxy)carbonyl, ($C_1$-$C_8$-alkylthio)carbonyl, ($C_1$-$C_4$-alkoxy-$C_1$-$C_4$-alkyl)carbonyl, ($C_3$-$C_6$-alkenyloxy)carbonyl, ($C_3$-$C_6$-alkynyloxy)-carbonyl, ($C_3$-$C_8$-cycloalkyl)carbonyl; ($C_1$-$C_6$-haloalkyl)carbonyl, ($C_1$-$C_6$-haloalkoxy)carbonyl, ($C_1$-$C_6$-haloalkylthio)carbonyl, (halo-$C_1$-$C_4$-alkoxy-$C_1$-$C_4$-alkyl)carbonyl, ($C_3$-$C_6$-haloalkenyloxy)carbonyl, ($C_3$-$C_6$-haloalkynyloxy)carbonyl, ($C_3$-$C_8$-halocycloalkyl)carbonyl having in each case 1 to 9 fluorine, chlorine and/or bromine atoms; or —$CH_2$—C≡C—$R^{1-A}$, —$CH_2$—CH=CH—$R^{1-A}$, —CH=C=CH—$R^{1-A}$, —C(=O)C(=O)$R^2$, —CONR$^3$R$^4$ or —CH$_2$NR$^5$R$^6$, $R^{1-A}$ represents hydrogen, $C_1$-$C_6$-alkyl, $C_1$-$C_6$-haloalkyl, $C_2$-$C_6$-alkenyl, $C_2$-$C_6$-alkynyl, $C_3$-$C_7$-cycloalkyl, ($C_1$-$C_4$-alkoxy)carbonyl, ($C_3$-$C_6$-alkenyloxy)carbonyl, ($C_3$-$C_6$-alkynyloxy)carbonyl or cyano, $R^2$ represents hydrogen, $C_1$-$C_8$-alkyl, $C_1$-$C_8$-alkoxy, $C_1$-$C_4$-alkoxy-$C_1$-$C_4$-alkyl, $C_3$-$C_8$-cycloalkyl; $C_1$-$C_6$-haloalkyl, $C_1$-$C_6$-haloalkoxy, halo-$C_1$-$C_4$-alkoxy-$C_1$-$C_4$-alkyl, $C_3$-$C_8$-halocycloalkyl having in each case 1 to 9 fluorine, chlorine and/or bromine atoms, $R^3$ and $R^4$ independently of one another each represent hydrogen, $C_1$-$C_8$-alkyl, $C_1$-$C_4$-alkoxy-$C_1$-$C_4$-alkyl, $C_3$-$C_8$-cycloalkyl; $C_1$-$C_8$-haloalkyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms, $R^3$ and $R^4$ furthermore together with the nitrogen atom to which they are attached form a saturated heterocycle which is optionally mono- or polysubstituted by identical or different substituents from the group consisting of halogen and $C_1$-$C_4$-alkyl and which has 5 to 8 ring atoms, where the heterocycle may contain 1 or 2 further non-adjacent heteroatoms from the group consisting of oxygen, sulphur and NR$^7$, $R^5$ and $R^6$ independently of one another each represent hydrogen, $C_1$-$C_8$-alkyl, $C_3$-$C_8$-cycloalkyl; $C_1$-$C_8$-haloalkyl, $C_3$-$C_8$-halocycloalkyl having in each case 1 to 9 fluorine, chlorine and/or bromine atoms, $R^5$ and $R^6$ furthermore together with the nitrogen atom to which they are attached form a saturated heterocycle which is optionally mono- or polysubstituted by identical or different substituents from the group consisting of halogen and $C_1$-$C_4$-alkyl and which has 5 to 8 ring atoms, where the heterocycle may contain 1 or 2 further non-adjacent heteroatoms from the group consisting of oxygen, sulphur and NR$^7$, $R^7$ represents hydrogen or $C_1$-$C_6$-alkyl,
$R^8$ represents hydrogen or fluorine,
$R^9$ represents —SO$_m$R$^{11}$, —SO$_2$NR$^{12}$R$^{13}$, —C(=X)R$^{14}$, —NR$^{12}$R$^{13}$, —CH$_2$—NR$^{12}$R$^{13}$,
$R^{10}$ represents fluorine, chlorine, bromine, iodine, methyl or trifluoromethyl,
$R^{11}$ represents $C_1$-$C_6$-alkyl or $C_1$-$C_6$-haloalkyl having 1 to 13 halogen atoms,
m represents 1 or 2,
$R^{12}$ represents hydrogen, $C_1$-$C_4$-alkyl or —C(=X)R$^{14}$,
$R^{13}$ represents hydrogen, $C_1$-$C_4$-alkyl or —C(=X)R$^{14}$,
$R^{12}$ and $R^{13}$ furthermore together with the nitrogen atom to which they are attached form a saturated heterocycle which is optionally mono- or polysubstituted by identical or different substituents from the group consisting of halogen and $C_1$-$C_4$-alkyl and which has 5 to 8 ring atoms, where the heterocycle may contain 1 or 2 further non-adjacent heteroatoms from the group consisting of oxygen, sulphur and NR$^7$,
X represents O (oxygen) or S (sulphur),
$R^{14}$ represents hydrogen, $C_1$-$C_4$-alkyl, $C_1$-$C_4$-alkoxy or —NR$^{16}$R$^{17}$,
$R^{15}$ represents hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylthio-$C_1$-$C_4$-alkyl or $C_1$-$C_6$-haloalkyl, where the three radicals $R^{15}$ may each be identical or different,
$R^{16}$ hydrogen or $C_1$-$C_4$-alkyl,
$R^{17}$ hydrogen or $C_1$-$C_4$-alkyl, R¹⁶ and R¹⁷ furthermore together with the nitrogen atom to which they are attached form a saturated heterocycle which is optionally mono- or polysubstituted by identical or different substituents from the group consisting of halogen and C₁-C₄-alkyl and which has 5 to 8 ring atoms, where the heterocycle may contain 1 or 2 further non-adjacent heteroatoms from the group consisting of oxygen, sulphur and NR⁷, A represents one of the radicals A1 to A19 below

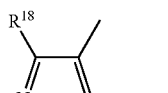
A1

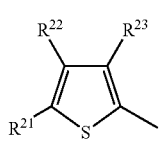
A2

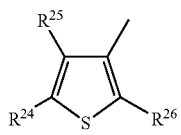
A3

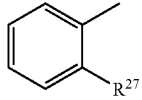
A4

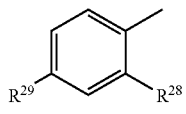
A5

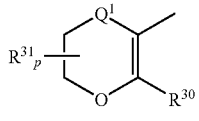
A6

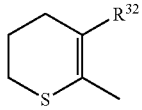
A7

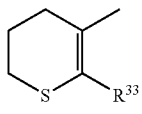
A8

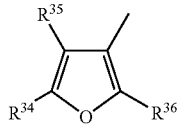
A9

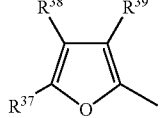
A10

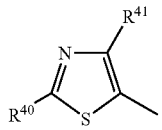
A11

-continued

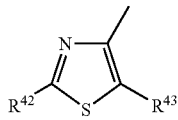
A12

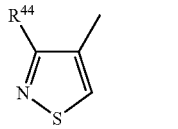
A13

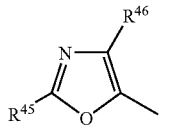
A14

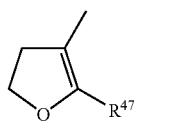
A15

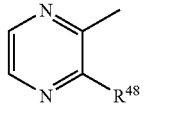
A16

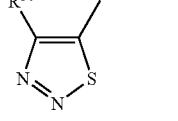
A18

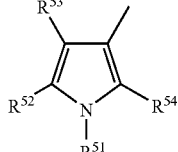
A19

R¹⁸ represents hydrogen, cyano, halogen, nitro, C₁-C₄-alkyl, C₁-C₄-alkoxy, C₁-C₄-alkylthio, C₃-C₆-cycloalkyl, C₁-C₄-haloalkyl, C₁-C₄-haloalkoxy or C₁-C₄-haloalkylthio having in each case 1 to 5 halogen atoms, aminocarbonyl or aminocarbonyl-C₁-C₄-alkyl, R¹⁹ represents hydrogen, halogen, cyano, C₁-C₄-alkyl, C₁-C₄-alkoxy or C₁-C₄-alkylthio, R²⁰ represents hydroxy-C₁-C₄-alkyl, C₂-C₆-alkenyl, C₃-C₆-cyclo-alkyl, C₁-C₄-alkylthio-C₁-C₄-alkyl, C₁-C₄-alkoxy-C₁-C₄-alkyl, C₁-C₄-haloalkyl, C₁-C₄-haloalkylthio-C₁-C₄-alkyl, C₁-C₄-haloalkoxy-C₁-C₄-alkyl having in each case 1 to 5 halogen atoms, or phenyl, R²¹ and R²² independently of one another represent halogen or C₁-C₄-haloalkyl having 1 to 5 halogen atoms, R²³ represents halogen, cyano, or C₁-C₄-haloalkyl or C₁-C₄-haloalkoxy having in each case 1 to 5 halogen atoms, R²⁴ and R²⁵ independently of one another represent halogen or C₁-C₄-haloalkyl having 1 to 5 halogen atoms, R²⁶ represents halogen or C₁-C₄-haloalkyl having 1 to 5 halogen atoms, R²⁷ represents hydrogen, hydroxyl, cyano, C₁-C₄-haloalkoxy or C₁-C₄-haloalkylthio having in each case 1 to 5 halogen atoms, R²⁸ represents halogen, hydroxyl, cyano, C₁-C₄-alkyl, C₁-C₄-alkoxy, C₁-C₄-alkylthio, C₁-C₄-haloalkyl, C₁-C₄-haloalkylthio or C₁-C₄-haloalkoxy having in each case 1 to 5 halogen atoms, R²⁹ represents hydrogen, halogen, cyano, C₁-C₄-alkyl, C₁-C₄-alkoxy, C₁-C₄-alkylthio, C₁-C₄-haloalkyl, C₁-C₄-haloalkoxy having in each case 1 to 5 halogen atoms, C₁-C₄-alkylsulphinyl or C₁-C₄-alkylsulphonyl, R³⁰ represents C₁-C₄-alkyl or C₁-C₄-haloalkyl having 1 to 5 halogen atoms, R³¹ represents C₁-C₄-alkyl, Q¹ represents S (sulphur), SO, SO₂ or CH₂, p represents 0, 1 or 2, where R²² represents identical or different radicals if p represents 2, R³² represents C₁-C₄-alkyl or C₁-C₄-haloalkyl having 1 to 5 halogen atoms, R³³ represents C₁-C₄-alkyl or C₁-C₄-haloalkyl having 1 to 5 halogen atoms, R³⁴ and R³⁵ independently of one another represent hydrogen, halogen, amino, C₁-C₄-alkyl or C₁-C₄-haloalkyl having 1 to 5 halogen atoms, R³⁶ represents hydrogen, halogen, C₁-C₄-alkyl or C₁-C₄-haloalkyl having 1 to 5 halogen atoms, R³⁷ and R³⁸ independently of one another represent hydrogen, halogen, amino, nitro, C₁-C₄-alkyl or C₁-C₄-haloalkyl having 1 to 5 halogen atoms, R³⁹ represents hydrogen, halogen, C₁-C₄-alkyl or C₁-C₄-haloalkyl having 1 to 5 halogen atoms, R⁴⁰ represents halogen, amino, C₁-C₄-alkylamino, di-(C₁-C₄-alkyl)amino, cyano, C₁-C₄-haloalkyl having 1 to 5 halogen atoms, R⁴¹ represents halogen, C₁-C₄-alkyl or C₁-C₄-haloalkyl having 1 to 5 halogen atoms, R⁴² represents hydrogen, halogen, amino, C₁-C₄-alkylamino, di-(C₁-C₄-alkyl)amino, cyano, C₁-C₄-alkyl or C₁-C₄-haloalkyl having 1 to 5 halogen atoms, R⁴³ represents halogen, C₁-C₄-alkyl or C₁-C₄-haloalkyl having 1 to 5 halogen atoms, R⁴⁴ represents halogen, C₁-C₄-alkyl or C₁-C₄-haloalkyl having 1 to 5 halogen atoms, R⁴⁵ represents hydrogen or C₁-C₄-alkyl, R⁴⁶ represents halogen or C₁-C₄-alkyl, R⁴⁷ represents C₁-C₄-alkyl or C₁-C₄-haloalkyl having 1 to 5 halogen atoms, R⁴⁸ represents hydrogen, halogen, C₁-C₄-alkyl or C₁-C₄-haloalkyl having 1 to 5 halogen atoms, R⁵⁰ represents C₁-C₄-alkyl, R⁵¹ represents hydrogen, cyano, C₁-C₄-haloalkyl having 1 to 5 halogen atoms, C₁-C₄-alkoxy-C₁-C₄-alkyl, hydroxy-C₁-C₄-alkyl, C₁-C₄-alkylsulphonyl, di(C₁-C₄-alkyl)aminosulphonyl, C₁-C₆-alkylcarbonyl or in each case optionally substituted phenylsulphonyl or benzoyl, R⁵² represents hydrogen, halogen, C₁-C₄-alkyl or C₁-C₄-haloalkyl having 1 to 5 halogen atoms, R⁵³ represents hydrogen, halogen, cyano, C₁-C₄-alkyl or C₁-C₄-haloalkyl having 1 to 5 halogen atoms, R⁵⁴ represents hydrogen, halogen, C₁-C₄-alkyl or C₁-C₄-haloalkyl having 1 to 5 halogen atoms.

2. A process for preparing biphenylcarboxamide according to claim 1, comprising reacting (a) a carbonyl halide of formula (II)

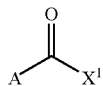
(II)

in which
X¹ represents halogen or hydroxyl,
with an amine of the formula (III)

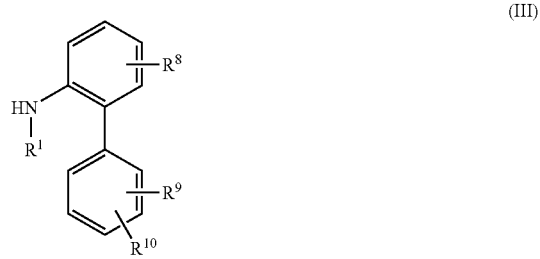
(III)

if appropriate in the presence of a coupling agent, if appropriate in the presence of an acid binder and if appropriate in the presence of a diluent, or (b) reacting a biphenylcarboxamide of formula (I-a)

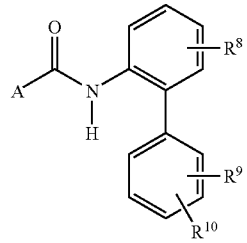
(I-a)

with a halide of formula (IV)

R¹⁻ᴮ-Hal     (IV)

in which

R¹⁻ᴮ represents C₁-C₈-alkyl, C₁-C₆-alkylsulphinyl, C₁-C₆-alkylsulphonyl, C₁-C₄-alkoxy-C₁-C₄-alkyl, C₃-C₈-cycloalkyl; C₁-C₆-haloalkyl, C₁-C₄-haloalkylthio, C₁-C₄-haloalkylsulphinyl, C₁-C₄-haloalkylsulphonyl, halogen-C₁-C₄-alkoxy-C₁-C₄-alkyl, C₃-C₈-halocycloalkyl having in each case 1 to 9 fluorine, chlorine and/or bromine atoms; formyl, formyl-C₁-C₃-alkyl, (C₁-C₃-alkyl)carbonyl-C₁-C₃-alkyl, (C₁-C₃-alkoxy)carbonyl-C₁-C₃-alkyl; halo-(C₁-C₃-alkyl)carbonyl-C₁-C₃-alkyl, halo-(C₁-C₃-alkoxy)carbonyl-C₁-C₃-alkyl having in each case 1 to 13 fluorine, chlorine and/or bromine atoms;

(C₁-C₈-alkyl)carbonyl, (C₁-C₈-alkoxy)carbonyl, (C₁-C₈-alkylthio)carbonyl, (C₁-C₄-alkoxy-C₁-C₄-alkyl)carbonyl, (C₃-C₆-alkenyloxy)carbonyl, (C₃-C₆-alkynyloxy)carbonyl, (C₃-C₈-cycloalkyl)carbonyl; (C₁-C₆-haloalkyl)-carbonyl, (C₁-C₆-haloalkoxy)carbonyl, (C₁-C₆-haloalkylthio)carbonyl, (halo-C₁-C₄-alkoxy-C₁-C₄-alkyl)carbonyl, (C₃-C₆-haloalkenyloxy)carbonyl, (C₃-C₆-haloalkynyloxy)carbonyl, (C₃-C₈-halocycloalkyl)carbonyl having in each case 1 to 9 fluorine, chlorine and/or bromine atoms; or —CH₂—C≡C—R¹⁻ᴬ, —CH₂—CH═CH—R¹⁻ᴬ, —CH═C═CH—R¹⁻ᴬ, —C(═O)C(═O)R², —CONR³R⁴ or —CH₂NR⁵R⁶, Hal represents chlorine, bromine or iodine in the presence of a base and in the presence of a diluent.

3. A composition for controlling an unwanted microorganism, comprising at least one biphenylcarboxamide according to claim 1 and an extender and/or surfactant.

4. A biphenylcarboxamide according to claim 1 for controlling an unwanted microorganism.

5. A method for controlling an unwanted microorganism, comprising applying a biphenylcarboxamide according to claim 1 to a microorganism and/or a habitat thereof.

6. A process for preparing a composition for controlling an unwanted microorganism, comprising mixing a biphenylcarboxamide according to claim 1 with an extender and/or a surfactant.

7. A biphenylcarboxamide according to claim 1 for treating a seed.

8. A biphenylcarboxamide according to claim 1 for treating a transgenic plant.

9. A biphenylcarboxamide according to claim 1 for treating a seed of a transgenic plant.

10. An Amine of formulae (III-1), (III-2) and (III-3)

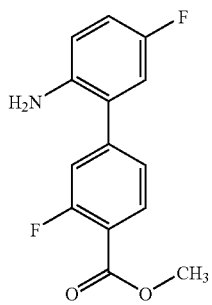
(III-1)

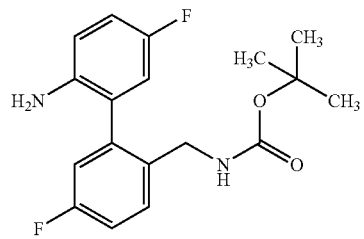
(III-2)

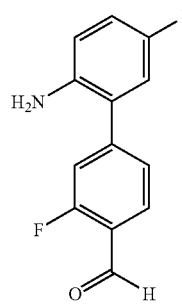
(III-3)

* * * * *